(12) United States Patent
Velander et al.

(10) Patent No.: US 6,984,772 B1
(45) Date of Patent: Jan. 10, 2006

(54) TRANSGENIC NON-HUMAN MAMMALS PRODUCING FIBRINOGEN IN THEIR MILK

(75) Inventors: William H. Velander, Blacksburg, VA (US); William N. Drohan, Springfield, VA (US); Henryk Lubon, Rockville, MD (US); John L. Johnson, Blacksburg, VA (US)

(73) Assignees: Virginia Tech Intellectual Properties, Inc., Blacksburg, VA (US); American Red Cross, Rockville, MD (US); The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 08/443,184

(22) Filed: May 17, 1995

Related U.S. Application Data

(63) Continuation-in-part of application No. 08/198,068, filed on Feb. 18, 1994, now abandoned.

(51) Int. Cl.
  C12P 21/00   (2006.01)
  A01K 67/00   (2006.01)
  C12N 15/00   (2006.01)

(52) U.S. Cl. .............................. 800/7; 800/14; 800/15; 800/16; 800/17; 800/18; 800/25

(58) Field of Classification Search ................ 800/2, 800/7, 14, 15, 16, 17, 18, 25; 435/172.3, 435/69.7, 69.8, 71.1, 69.1, 69.6, 325, 352, 435/354; 536/23.1, 23.5

See application file for complete search history.

(56) References Cited

U.S. PATENT DOCUMENTS

| | | | |
|---|---|---|---|
| 4,873,316 A | 10/1989 | Meade et al. | 530/412 |
| 5,304,489 A | 4/1994 | Rosen | 435/320.1 |

FOREIGN PATENT DOCUMENTS

| | | |
|---|---|---|
| EP | 0 264 166 | 4/1988 |
| WO | 88/00239 | 1/1988 |
| WO | 88/01648 | 3/1988 |
| WO | WO A-92 11757 | 7/1995 |

OTHER PUBLICATIONS

Danishefsky et al. Intracellular Fate of Fibrinogen B–beta Chain Expressed in COS Cells. Biochim. Biophys. Acta. 1990, vol. 1048, pp. 202–208.*
Roy et al. Assembly and Secretion of Recombinant Human Fibrinogen. J. Biol. Chem. Mar. 15, 1991, vol. 266, No. 8, pp. 4758–4763.*
Chung, et al., "γ and γ' Chains of Human Fibrinogen Are Produced by Alternative mRNA Processing", Biochemistry 1984, 23, 4232–4326.
Roy, et al., "Assembly and Secretion of Recombinant Human Fibrinogen", Journal of Biological Chemistry, vol. 266, No. 8, 1991, pp. 4758–4763.
Chung, et al., "Characterization of Complementary Deoxyribonucleic Acid and Genomic Deoxyribonucleic Acid for the β Chain of Human Fibrinogen", Biochemistry 1983, 22, pp. 3244–3250.
Chung, et al., "Characterization of a Complementary Deoxyribonucleic Acid Coding for the γ Chain of Human Fibrinogen", Biochemistry 1983, 22, pp. 3250–3256.
Rixon, et al., "Characterization of a Complementary Deoxyribonucleic Acid Coding for the α Chain of Human Fibrinogen", Biochemistry 1983, 22, pp. 3237–3244.
Farrell, et al., "Recombinant Human Fibrinogen and Sulfation of the γ' Chain", Biochemistry 1991, 30, pp. 9414–9420.
Hartwig, et al., "Studies on the Assembly and Secretion of Fibrinogen", The Journal of Biological Chemistry, vol. 266, No. 10, 1991, pp. 6578–6585.
Huang, et al., "Biosynthesis of Human Fibrinogen", The Journal of Biological Chemistry, vol. 268, No. 12, 1993, pp. 8919–8926.
Farrell, et al., "Processing of the Carboxyl 15–Amino Acid Extension in the α–Chain of Fibrinogen", The Journal of Biological Chemistry, vol. 268, No. 14, 1993, pp. 10351–10355.
Lord, et al., "Purification and Characterization of Recombinant Human Fibrinogen", Blood Coagulation and Fibrinolysis, vol. 4, 1993, pp. 55–59.
Binnie, et al., "Characterization of Purified Recombinant Fibrinogen: Partial Phosphorylation of Fibrinopeptide A", Reprinted from Biochemistry, 1993, 32, pp. 107–113.
Lord, "Expression of a Cloned Human Fibrinogen cDNA in *Escherichia coli*: Synthesis of an A Alpha Polypeptide", DNA, vol. 4, No. 1, 1985, pp. 33–38.
Boylard, et al., "Expression in *Escherichia coli* of the Human Fibrinogen Bβ Chain and Its Cleavage by Thrombin", Blood, vol. 73, No. 5, 1989, pp. 1202–1206.
Imam, et al., "Isolation and Characterisation of cDNA Clones of the Aα and γ–chains of Human Fibrinogen", Nucleic Acids Research, vol. 11, No. 21, 1983, pp. 7427–7435.
Kant, et al., "Partial mRNA Sequences for Human Aα, Bβ, and γ Fibrinogen Chains: Evolutionary and Functional Implications", Proc. Natl. Acad. Sci. USA, vol. 80, 1983, pp. 3953–3957.

(Continued)

*Primary Examiner*—Deborah Crouch
(74) *Attorney, Agent, or Firm*—Foley & Lardner LLP

(57) ABSTRACT

A transgenic, non-human mammalian animal is capable of expressing a heterologous gene for human or other recombinant physiologically functional fibrinogen holoprotein or individual subunit chain polypeptides thereof or a modified or fusion fibrinogen in mammary glands of the animals and secreting the expressed product into a body fluid. Methodology employing such a mammal yields recombinant physiologically functional fibrinogens, subunit chain polypeptides thereof, and modified or fusion fibrinogens.

38 Claims, 11 Drawing Sheets

OTHER PUBLICATIONS

Cecil Textbook of Medicine, 1988, W.B. Saunders Company, Philadelphia, J.B. Wyngaarden et al. 18th Ed., vol. 1, pp. 1061, 1063–1064, 1071–1074.

Prunkard et al. "Expression of Recombinant Human Fibrinogen in the Milk of Transgenic Mice", *Fibrinolysis*, 8(1): 102 (1994)/Abstract 285.

Lee et al. Production of Biomedical Proteins in the Milk of Transgenic Dairy Cows: The State Of The Art:, *J. Controlled Release*, 29: 213–221 (1994).

Lord et al. "Purification and Characterization of Recombinant Human Fibrinogen", *Blood Coagulation and Fibrinolysis*, 4: 55–59 (1993).

Roy et al. Assembly and Secretion of Recombinant Human Fibrinogen, *J. Biological Chemistry* 266(8): 4758–4763 (1991).

Rixon et al. "Characterization of a Complementary Deoxyribonucleic Acid Coding for the Alpha Chain of Human Fibrinogen", *Biochemistry* 22: 3237–3244 (1983).

Chung et al. "Characterization of a Complementary Deoxyribonucleic Acid Coding for the Gamma Chain of Human Fibrinogen", *Biochemistry* 2: 3250–3256 (1983).

Chung et al. "Characterization of Complementary Deoxyribonucleic Acid and Genomic Deoxyribonubleic Acid For The Beta Chain of Human Fibrinogen", *Biochemistry* 22: 3244–3250 (1983).

* cited by examiner

WESTERN BLOT (UNDER NON-REDUCING CONDITIONS)

| LANE | SAMPLE |
|---|---|
| 1. | hfib, 100 ngs |
| 2. | TG 1-11-4 (pellet-2), 15 ngs |
| 3. | TG 1-11-4 (pellet-2), 15 ngs |
| 4. | TG 1-6-9 (pellet-2), 30 ngs |
| 5. | TG 1-6-9 (pellet-2), 30 ngs |
| 6. | DIAFILTERED MOUSE PLASMA, 1-2 μgs |
| 7. | NTG (pellet-2), 600 ngs |
| 8. | hfib, 10 ngs |

WESTERN BLOT (SDS-PAGE UNDER REDUCING CONDITIONS)

| LANE | SAMPLE |
|---|---|
| 1. | HUMAN FIBRINOGEN (100 ngs) |
| 2. | hFib (50 ngs) |
| 3. | hFib (10 ngs) |
| 4. | MOUSE PLASMA DERIVATIVE (200 ngs) |
| 5. | TG WHEY (pellet-2) 60 ngs |
| 6. | TG WHEY (pellet-2) 30 ngs |
| 7. | TG WHEY (pellet-2) 15 ngs |
| 8. | TG WHEY (pellet-2) 8 ngs |

TRANSGENIC NON-HUMAN MAMMALS PRODUCING FIBRINOGEN IN THEIR MILK

The present application is a continuation-in-part of U.S. Ser. No. 08/198,068, filed on Feb. 18, 1994, now abandoned.

BACKGROUND OF THE INVENTION

The present invention relates in general to the use of transgenic animals to produce therapeutically useful amounts of clinically important recombinant proteins. More particularly, this invention relates to the production in transgenic animals of clinically useful quantities of the blood clotting protein, fibrinogen ("FIB").

The ultimate event in the blood clotting cascade is the thrombin-catalyzed conversion of FIB ($M_r$=340,000) to fibrin ($M_r$=329,000), the latter forming the fibrin clot. FIB deficiency is generally transmitted as an autosomal recessive trait and may manifest as a complete or partial absence of FIB from the blood plasma. Clinically, the disease resembles moderate or mild hemophilia. Congenital fibrinogen abnormality may be due to the hereditary synthesis of structurally or functionally abnormal molecules, as in Vlissingen, Ijmuiden and Nijmegen fibrinogens. An acquired deficiency of this protein may occur due to impaired hepatic synthesis of the protein, as occurs, for example, in hepatitis or hepatic necrosis, or to accelerated destruction of the protein caused, for example, by increased blood proteolytic activity.

Control of bleeding in such patients is currently achieved by transfusion of FIB contained in freshly-frozen human plasma or in concentrates of the protein isolated from donor blood. While these replacement therapies are generally effective, they place patients at risk for virus-transmissible diseases such as hepatitis or AIDS. Although this risk has been greatly reduced by inactivating such viruses with heat or organic solvents, such preparations have greatly increased the cost of treatment, and are not risk free. There is thus a critical need for a source of this protein alternate to human plasma.

An important advance in obtaining an alternate clinical source of FIB has been the cloning of cDNAs encoding the three different fibrinogen chains, and the publication of cDNA sequences. Rixon et al., *Biochemistry* 22: 3237 (1983); Chung et al., ibid: 3244; Chung et al., ibid: 3250. The structure of the FIB molecule is exceedingly complex. Each molecule of FIB consists of two sets of three different polypeptide chains, designated A$\alpha$, B$\beta$ and G$\gamma$, with molecular masses of 66 kDa, 52 kDa and 46.5 kDa, respectively. The two half-molecules containing each set of chains are linked together by three disulfide bonds. In addition, a complex set of intra- and inter-chain disulfide bonds (there are a total of 29 disulfide bonds with no free sulfhydryl groups) are involved in maintaining proper functional structure. Further, FIB is a glycoprotein with highly specific glycosylations. The molecule contains four carbohydrate chains, one each on the B, $\beta$, G and $\gamma$ chains; the $\alpha$ and A chains contain no carbohydrate. About 11 kDa of the total molecular mass of FIB (340 kDa) is attributable to this carbohydrate, added to the molecule post-translationally. In addition, isoforms of glycoproteins are known corresponding to differences in sialic acids on the carbohydrate chains. Proper carbohydrate modification is required for functional activity of FIB.

These highly complex characteristics of the functional FIB molecule has made unpredictable and difficult the expression, assembly and secretion of fully formed and functional recombinant molecules. A cDNA encoding the human FIB A$\alpha$ chain has been expressed in bacteria. Lord, *DNA* 4:33 (1985). This is of limited usefulness, however, since the other fibrinogen chains that bear carbohydrates cannot be produced in prokaryotes.

Individual FIB chains have been expressed in COS1 (transformed monkey kidney fibroblast) cells. Danishevsky et al., *Biochim. Biophys. Acta* 1048: 202 (1990). In addition, transfecting COS1 cells with a combination of cDNAs encoding the individual human fibrinogen subunit chains is reported to produce the holoprotein, but the amounts produced were small, and substantially less than the production achieved in the transgenic animal systems to be described below. Roy et al., *J. Biol. Chem.*, 266: 4758 (1991). The secretion of partially assembled or wholly unassembled and separate human FIB ("hFIB") or recombinant human FIB ("rhFIB") chains has not been reported for native or genetically engineered tissues. Chung et al. (1983); Danishevsky et al (1990). In addition, there are serious drawbacks to the use of mammalian cell tissue culture systems for production of FIB. These include the high costs of growth media, the labor intensive nature of such systems, and limited production capacity.

An important need persists for an efficient and relatively inexpensive means of producing clinically useful amounts of infectious particle-free rhFIB protein. The present invention satisfies this need. It has been surprisingly found that transgenic animals can be genetically engineered to produce and secrete into readily accessible body fluids therapeutically useful quantities of rhFIB. In addition to therapeutic uses involving replacement or addition therapy, the FIB of the invention finds us in a variety of applications, such as a "glue" in surgical procedures, as a delivery system for drugs, such as antibiotics or anti-parasitic agents, to wounds, as a food substitute, and for altering the composition of milk. These transgenic systems are described below.

SUMMARY OF THE INVENTION

In accordance with the present invention, there is provided a non-human mammalian animal that has stably integrated into its genome heterologous (that is, exogenously derived) polynucleotides that encode the A$\alpha$, B$\beta$ and G$\gamma$ polypeptide chains of human FIB, and that direct by means of regulatory and signal sequences the expression of biologically active rhFIB in mammary gland cells, such that newly synthesized fibrinogen is secreted into bodily fluid compartments, particularly milk, blood or urine of the animal. By integrating fewer than all of the three heterologous polynucleotides, individual chains of fibrinogen can be produced and may be secreted. By integrating heterologous polynucleotides that have been modified prior to administration to the host animal, modified FIB and products thereof can be produced.

It therefore is an object of the present invention to provide transgenic animals capable of producing rhFIB, individual polypeptide subunit chains of FIB, or FIB-derived proteins and protein products.

It is also an object of the invention to provide a means of producing rhFIB, individual polypeptide subunits thereof, or FIB-derived proteins and protein products in transgenic animals.

In a preferred embodiment of this aspect of the invention, lactating transgenic animals produce the rhFIB, individual FIB subunits or FIB-derived proteins in their mammary glands and secrete these products in their milk. In another preferred embodiment, transgenic animals secrete the produced rhFIB, individual FIB subunits, or FIB-derived proteins in their blood and/or urine.

DETAILED DESCRIPTION OF PREFERRED EMBODIMENTS

Figure 1:
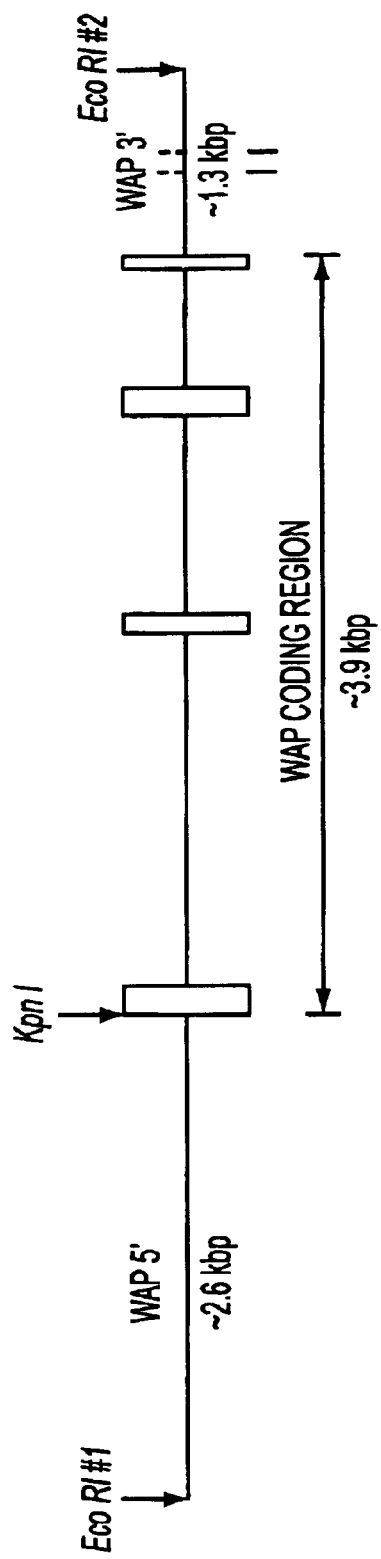
FIG. 1 is a sketch of the murine WAP gene.

An approach has been discovered to producing non-human, transgenic mammalian animals that are genetically engineered to secrete, into readily accessible body fluids such as milk, blood and urine, recombinant holofibrinogen (for example, rhFIB), individual subunit chain polypeptides of FIB, and modified FIB subunit chains in amounts and in forms that are suitable for treating humans with genetic or acquired deficiencies of the normal protein.

Glossary

The term "animal" here denotes all mammalian animals except humans. It also includes an individual animal in all stages of development, including embryonic and fetal stages. A "transgenic" animal is any animal containing cells that bear genetic information received, directly or indirectly, by deliberate genetic manipulation at the subcellular level, such as by microinjection or infection with recombinant virus.

"Transgenic" in the present context does not encompass classical crossbreeding or in vitro fertilization, but rather denotes animals in which one or more cells receive a recombinant DNA molecule. Although it is highly preferred that this molecule be integrated within the animal's chromosomes, the present invention also contemplates the use of extrachromosomally replicating DNA sequences, such as might be engineered into yeast artificial chromosomes.

The term "germ cell line transgenic animal" refers to a transgenic animal in which the genetic information has been taken up and incorporated into a germ line cell, therefore conferring the ability to transfer the information to offspring. If such offspring in fact possess some or all of that information, then they, too, are transgenic animals.

The information to be introduced into the animal is preferably foreign ("heterologous") to the species of animal to which the recipient belongs, but the information also may be foreign only to the particular individual recipient, or genetic information already possessed by the recipient. In the last case, the introduced gene may be differently expressed than is the native gene.

By "holofibrinogen" is meant the mature, fully glycosylated, physiologically functional fibrinogen. Unless specified otherwise, the abbreviations FIB or hFIB or hrFIB as used herein will refer to this holoprotein.

Animals

The transgenic animals of this invention may be any animal, other than human, that produces milk, blood serum, and urine. Farm animals (pigs, goats, sheep, cows, horses, rabbits and the like), rodents (such as mice), and domestic pets (for example, cats and dogs) are included in the scope of the present invention.

Stable Integration of DNA Constructs in Animal Genome

It is highly preferred that the transgenic animals of the present invention be produced by introducing into single cell embryos appropriate polynucleotides that encode human holoFIB, or individual subunit chain polypeptides or modified products thereof, in a manner such that these polynucleotides are stably integrated into the DNA of germ line cells of the mature animal and inherited in normal mendelian fashion.

Advances in technologies for embryo micromanipulation now permit introduction of heterologous DNA into fertilized mammalian ova. For instance, totipotent or pluripotent stem cells can be transformed by microinjection, calcium phosphate mediated precipitation, liposome fusion, retroviral infection or other means, the transformed cells are then introduced into the embryo, and the embryo then develops into a transgenic animal. In a preferred method, developing embryos are infected with a retrovirus containing the desired DNA, and transgenic animals produced from the infected embryo. In a most preferred method, however, the appropriate DNAs are coinjected into the pronucleus or cytoplasm of embryos, preferably at the single cell stage, and the embryos allowed to develop into mature transgenic animals. Those techniques as well known. For instance, reviews of standard laboratory procedures for microinjection of heterologous DNAs into mammalian (mouse, pig, rabbit, sheep, goat, cow) fertilized ova include: Hogan et al., MANIPULATING THE MOUSE EMBRYO, Cold Spring Harbor Press, 1986; Krimpenfort et al., *Bio/Technology* 9:844 (1991); Palmiter et al., *Cell* 41: 343 (1985); Kraemer et al., GENETIC MANIPULATION OF THE EARLY MAMMALIAN EMBRYO, Cold Spring Harbor Laboratory Press, 1985; Hammer et al., *Nature*, 315: 680 (1985); Purcel et al., *Science*, 244: 1281 (1986); Wagner et al., U.S. Pat. No. 5,175,385; Krimpenfort et al., U.S. Pat. No. 5,175,384, the respective contents of which are incorporated by reference. The human FIB or FIB subunit genes can be obtained by isolating them from an appropriate genomic source (i.e., human liver, which is the natural organ for production of this protein) by alternate methods which include preparation of cDNAs from isolated mRNA templates, direct synthesis, or some combination thereof. The cDNAs encoding individual FIB chains can be fused, in proper reading frame, with appropriate regulatory signals as described in detail below, to produce a genetic construct that is then amplified, for example, by preparation in a bacterial vector, according to conventional methods. See, for example, the standard work: Sambrook et al., MOLECULAR CLONING: A LABORATORY MANUAL, Cold Spring Harbor Press, 1989, the contents of which are incorporated by reference. The amplified construct is thereafter excised from the vector and purified for use in producing transgenic animals. Purification can be accomplished by means of one or more cycles of anionic HPLC; alternate techniques include ultracentrifugation through a sucrose or NaCl gradient, gel electroelution followed by agarose treatment and ethanol precipitation, or low pressure chromatography. Purification by several cycles of HPLC allows for remarkably high transformation frequencies, on the order of 20% or more in both mice and pigs.

Although the present invention preferably entails the use of DNA constructs that produce the desired or native human FIB per se, the desired protein may also be produced as a fusion protein containing another protein. For example, the desired recombinant FIB protein of this invention may be produced as part of a larger recombinant protein in order to stabilize the desired protein or to make its purification from milk faster and easier. The fusion partners are then separated chemically or enzymatically, and the desired FIB isolated. Production of a fusion product between FIB and β-lactoglobulin (BLG) or between FIB and another milk protein are contemplated.

The rhFIB may also be produced having the identical sequence as the native molecule, or it may be produced as a fragment or derivative. A variety of modified rhFIB or subunits thereof can be produced by altering a cloned DNA using the well-known techniques of in vitro mutagenesis such as those set out in the references above.

Production of transgenic animals containing the gene for human FIB involves the use of cDNA or genomic DNA that encodes the α, β, and γ chains of hFIB. See Rixon et al., 1983, and Chung et al., 1983, supra. The full-length base sequence of each chain is provided in these references, the contents of which therefore are incorporated by reference.

DNA constructs useful in the present invention provide a double stranded DNA sequence encoding FIB operably linked to all of the cis-acting signals necessary for mammary gland-specific expression of this protein, post-translational glycosylation of two of the three sets of chains of FIB (Bβ and Gγ), secretion of FIB into milk or other body fluids, and expression of full biological activity. As set out above, polynucleotides encoding FIB or FIB subunit chains suitable for use in the invention can be isolated by standard techniques starting from the known polynucleotide sequences.

Modified FIB DNA sequences also can be employed in this invention. Useful modifications within this context include, but are not limited to, those that alter post-translational modifications, size or active site of FIB, or that fuse this protein or portions thereof to another protein. Such modifications can be introduced into the protein by techniques well known in this art, such as by synthesizing modified genes by ligation of overlapping oligonucleotide or introducing mutations into the cloned genes by, for example, oligonucleotide-mediated mutagenesis. See, for example, Ebert et al., Bio/Technology 9: 835 (1991), Denman et al., loc. cit.: 839 (1991), and Gerard et al., Science 248: 1421 (1991), for details of procedures for site mutagenesis of proteins. One or more FIP glycosylation sites can be eliminated or changed by site mutagenesis, for instance. Another variant might be a chimeric FIB having a tissue growth factor as protease inhibitor peptide attached to the nascent FIP polypeptide during transgenic biosynthesis or by co-current translation. The assembly of the complex hexameric structure may be exploited to include a guest molecule, but while maintaining recognition of the FIB complex for secretion. Specific changes of entire domains within FIB could be used to impact specialized activity of other molecules, but still remain the hexameric structure required for secretion.

The cis-acting regulatory regions useful in the invention include the promoter that drives expression of the FIB or FIB subunit chain genes. Highly preferred are promoters that are specifically active in mammary gland cells and that involve milk proteins. Among such promoters, highly preferred are the whey acidic protein (WAP), short and long α, β and kappa casein, α-lactalbumin and β-lactoglobulin ("BLG") promoters. Promoters may be selected on the basis of the protein compositions of various milks.

For example, the WAP and BLG promoters are particularly useful with transgenic rodents, pigs and sheep. The rodent WAP short and long promoters have been used to express the rat WAP gene, the human tPA gene and the CD4 gene, while the sheep BLG promoter has been used to express the sheep BLG gene, the human alpha-1-antitrypsin gene and the human Factor IX gene. For reviews, see Paleyanda et al. in RECOMBINANT TECHNOLOGY IN HEMOSTASIS AND THROMBOSIS (eds. Hoyer et al.), Plenum Press, NY (1991), at page 197; Clark et al., TIBTECH 5: 20 (1987), the respective contents of which are incorporated by reference. Preferred among the promoters for carrying out the present invention are the rodent casein and WAP promoters (see, for example, Rosen, U.S. Pat. No. 5,304,489, and Meade, U.S. Pat. No. 4,873,316) and the casein, α-lactalbumin and BLG promoters (Strijker et al., U.S. Pat. Nos. 5,322,775 and 5,366,864) from porcine, bovine, equine and ovine (pigs, sheep, goats, cows, horses), rabbits, rodents and domestic pets (dogs and cats); accordingly, the respective contents of the aforementioned patents are incorporated by reference. The genes for these promoters have been isolated and their characterizations published. For reviews see Clark et al. (1987), supra, and Henninghausen, Protein Expression and Purification 1: 3 (1990). The mouse WAP promoter is commercially available; see ATCC catalogue no. 63005 (2d ed., 1991), Rockville, Md.

The promoter may be isolated by carrying out conventional restriction endonuclease and subcloning steps. A preferred mouse WAP promoter can be isolated as a 2.6 kb EcOR1-Kpn1 fragment which is immediately 5' to the WAP signal sequence. The "long" WAP promoter—the 5' 4.2 kb Sau3A-Kpn1 promoter of the mouse WAP gene, or a fragment thereof—is also suitable for carrying out the present invention (see, Paleyanda et al, 1991 above; Henninghausen, 1990, above).

Important to the present invention are regulatory sequences that direct secretion of proteins into milk and/or other body fluids of the transgenic animal. In this regard, both homologous and heterologous regulatory sequences are useful in the invention. Generally, regulatory sequences known to direct the secretion of milk proteins, such as either signal peptides from milk for production of individual FIB subunit chain polypeptides or the nascent target polypeptide for production of the holoFIB, can be used. Signal sequences also can be used in accordance with this invention that direct the secretion of expressed proteins into other body fluids, particularly blood and urine, such as signal sequences for coagulation proteins such as protein C and Factor VIII.

Unexpectedly, it has been found that a trigenic animal can efficiently express three separate transgenes which do not have a signal peptide operably linked between promoter and encoding DNA sequences, but still direct synthesis and secretion of a assembled recombinant human fibrinogen protein in milk of a transgenic animal. This occurs in a temporally regulated way as to enable a complex asymmetric assembly of the fibrinogen polypeptides which nascent polypeptides then enables subsequent secretion of the hexameric, 340 kDa protein in milk. It is important to note that, in general, mammalian cells do not efficiently secrete separate fibrinogen chains. See Danishefsky et al., *Biochim. Biophys. Acta* 1048: 202 (1990), and Hartwig et al., *J. Biol. Chem.*, 266: 6578 (1991). This phenomenon has been explained by Danishefsky et al. to be a consequence of proper folding rather than the presence of a specific domain within one of the component chains that may be a prerequisite for fibrinogen secretion; this, since neither of the three chains of fibrinogen by themselves have the integral signal for secretion. A separate, identifiable signal sequence therefore does not appear to exist in any of the individual $\alpha$, $\beta$ and $\gamma$ polypeptides (and, hence, there is no signal sequence encoded immediately preceding the coding sequence for any of the nascent polypeptides in the cDNA or genomic sequences of fibrinogen chains) for directing secretion. Importantly, it has been discovered that it is not necessary to add any coding sequence for milk protein or other specific signal sequences to the fibrinogen cDNAs used to make trigenic mice, pigs and cows which secrete properly folded and active transgenic hFIB. The highly preferred constructs consist of three separate transgenes; each transgene has the 2.5 kb-WAP-promoter ligated directly to the native cDNA for one the $\alpha,\beta$, and $\gamma$ FIB polypeptides with no intervening signal sequence.

As noted above, there is no requirement for a coding DNA for signal peptide sequences in each of the present three FIB polynucleotide constructs when producing holoFIB. The prior art does not suggest this fact, nor does it present a properly folded, complex recombinant fibrinogen structure which specifically enables the mammary tissue Golgi transport system to efficiently secrete the assembled FIB. The present examples have three salient features which show that indeed the mammary tissue can perform such a task. First, the levels of rFIB found are consistent with the stable expression levels found for prior examples of 2.5 kb 5'-WAP promoter-cDNA single gene, single polypeptide expressions in the milk of transgenic mice (i.e., about 1–100 µg/ml; Hennighausen et al., above). Second, the transgenic mice secrete fibrinogen without involution as indicated by their normal lactation and pup weight gain. Third, the recombinant fibrinogen secreted is physiologically active. Thus, in combination, these results suggest that no significant intracellular buildup of assembled fibrinogen occurs in the mammary epithelium which is sufficient to halt lactation. Likewise, no appreciable secretion of individual unassembled polypeptides occurred in trigenic-$\alpha$, $\beta$, $\gamma$-fibrinogen mice.

In contrast to the trigenic animal, it appears that a signal peptide is needed for each cDNA sequence encoding $\alpha$, $\beta$ and $\gamma$ if the unassembled, individual chains are to be efficiently secreted from the mammary epithelium.

Among the useful sequences that regulate transcription, in addition to the promoters discussed above, are enhancers, splice signals, transcription termination signals, and polyadenylation sites. Particularly useful in this regard are those that increase the efficiency of the transcription of the genes for fibrinogen in the mammary gland cells of the transgenic animals listed above. Preferred are transcription regulatory sequences for proteins highly expressed in the mammary gland cells (see above).

Preferably, the expression system or construct of this invention also includes a 3' untranslated region downstream of the DNA sequence encoding the desired recombinant protein, or the milk protein gene used for regulation. This region apparently stabilizes the RNA transcript of the expression system and thus increases the yield of the desired protein. Among the 3' untranslated regions useful in this regard are sequences that provide a poly A signal. Such sequences may be derived, for example, from the SV 40 small t antigen, from the casein 3' untranslated region, and from other 3' untranslated sequences well known in this art. Preferably, the 3' untranslated region is derived from a milk-specific protein. The stabilizing effect of this region's poly A transcript is important in stabilizing the mRNA of the expression sequence. Also important in increasing the efficiency of expression of FIB are ribosome binding sites. Likewise, sequences that regulate the post-translational modification of FIB subunits are useful in the invention.

Pursuant to the present invention, therefore, a double-stranded chimeric DNA, including genes that code for the FIB subunit chains and that are operably linked to cis-acting regulatory sequences which promote efficient expression of the former in milk and/or other body fluids, are introduced into an embryo, where they are integrated into the embryonic genome and become part of the inheritable genetic endowment of all of the animals cells, including the germ line cells, of the adult which matures from the embryo. The FIB thus expressed and secreted into milk is immunologically reactive, as measured by an ELISA assay described below.

Where the synthesis of a FIB subunit chain may be limiting in the production of the holoprotein, expression of this chain an be increased by placing the gene in a different genomic locus. This other locus can contain a DNA sequence under the same or a different regulatory sequence than the other two FIB sequences.

In a particularly preferred embodiment the transgenes of the invention generally consist of milk protein upstream and downstream and flanking sequences in combination, separately, with each of the three translated portions of the cDNA sequences representing the three FIB subunit chains. A native 5'-WAP regulatory sequence ending in an accessible restriction site immediately before/at the ATG codon may be ligated to each of the respective restriction sites which occur at the ATG of translatable sequences with no linker sequences derived from the chains of human FIB. A restriction site may be made through site mutagenesis of three bases located in each 3'-untranslatable sequences of the three FIB cDNAs. This preserves the stop sequence while adding a restriction site immediately after each of the translatable sequences of the FIB cDNAs. Each of the combined 5'-regulatory and FIB translatable sequences which end in a particular restriction site then can be ligated to a corresponding restriction site which occurs at the beginning of the 3'-untranslated region of WAP and adjoining WAP 3'-flanking region. This construction motif enables native 5'-regulatory and 3'-UTR of the milk protein genes to be immediately juxtaposed without intervening sequences (but see above relating to the insertion of the B$\beta$ gene at a different locus). Particular restriction sites at the ends of all constructs may be selected in order to facilitate concatenation of A$\alpha$, B$\beta$ and G$\gamma$ constructs into a single domain within the animal genome.

Although the foregoing, general description of the DNA constructs within the present invention relates in several places to the WAP promoter, it is emphasized that other suitable promoters (see above for discussion) can be ligated to the fibrinogen encoding polynucleotides in a similar manner. By way of illustration, the following discussion describes the use of the bovine lactoglobulin ("BLG") promoter to increase the efficiency of expression of FIB and FIB-BLG fusion proteins in mammary glands.

Using techniques described above, fibrinogen encoding cDNA may be inserted into an ovine BLG gene. In order to produce such a construction, for instance, the 11.2 Kbp ovine BLG gene may be modified to possess a unique EcoRV site upstream of the initiator ATG codon in the vector pUCXSRV. The sequence around this region is changed as follows:

```
                              PvuI       MetLys
Seq. ID No. 1 Natural  CCCCAGCTGCAGCCATGAAG EcoRV      MetLys
Seq. ID No. 2 pUCXSRV  CCCCAGGGATATCCCTGCAGCCATGAAG
```

This allows the cloning of blunt end fragments upstream of the BLG gene. The 1.5 kbp fragment from a plasmid (e.g., pWAP FIB) which contains a cDNA encoding human fibrinogen is isolated, blunt ends are generated with T4 DNA polymer, and the product is ligated to EcoRV-cleaved pUCXSRV. Following transformation of *E. coli* with this plasmid, clones that are produced can be characterized by restriction analysis of plasmid DNA prepared by a mini-prep method and by determination of the nucleotide sequence around the 5' and 3' cloning junctions for the DNA. Clones having the desired structure can be used to produce transgenic rodents, pigs, sheep, cows, horses and other farm animals and domestic pets (cats and dogs) that secrete a FIB-BLG fusion product into their biological fluids as described below.

A hFIB genomic sequence also may be fused to the ovine BLG promoter illustrated in the following discussion. DNA sequences encoding ovine BLG in plasmid pUCXSRV are deleted to generate a vector containing only ovine BLG promoter sequences(pUCSV). As with pUCSRV, blunt-ended fragments can be fused to this promoter region by ligation to a unique EcoRV site. The sequences 5' to this site are identical in both plasmids.

Genomic FIB sequences of greater than about 15 kbp can be introduced into transgenic animals, despite their length, through the use of cosmids with overlapping FIB sequences, whereupon the necessary assembly of an entire genomic polynucleotide encoding hFIB is achieved by homologous recombination in vivo after microinjection into an embryo cell. In constructs useful in the foregoing example, a plasmid in which the FIB genomic sequences are fused to ovine BLG 3' flanking sequences just after the fibrinogen translation termination codon to ensure proper transcription, termination and polyadenylation. The hFIB gene fused to ovine BLG 3' flanking sequences is excised from the plasmid, the 3' overhangs repaired using Klenow enzyme, and the product ligated to EcoRV-cleaved pUCSR. Following transformation of *E. coli*, the resulting clones are characterized by restriction DNA analysis and by determining the nucleotide sequences around the 5' and 3' cloning junctions. Clones having the desired structure may be introduced into fertilized animal ova for production of transgenic animals.

A variety of vectors based on the BLG gene may be constructed. In constructs based on this approach, the sequences encoding the ovine BLG protein are deleted, but the 5' promoter sequences are retained. Each may possess a different complement of introns from the ovine gene and a unique EcoRV site allowing the cloning of blunt ended fragments between the promoter and 3' flanking region of the gene. However, each contains the BLG promoter, the EcoRV site and the BLG 3'-flanking sequence. For each recombinant, the 1.5 kbp KpnI fragment from pWAP FIB is isolated, blunt ends generated as above, and the product ligated to EcoRV-cleaved vector sequences. Those constructs with the proper structures, determined as described above, can be used to express FIB in the biological fluids of transgenic animals.

A notable result is obtained with doubly-transgenic mice that are produced having native BLG genomic sequences which were injected as separate constructs to be concatenated in vivo, as additional flanking sequences to the BLG target cDNA construct (such as, BLG promoter-Intron I-EcoRV-Intron VI-BLG 3' flank plus BLG). In particular, such mice give higher expression more frequently than do mice produced using constructs of the BLG promoter-FIB cDNA-BLG gene or BLG promoter-FIB genomic (±BLG 3' end). Intact or native BLG genomic sequences that are preligated to the BLG-cDNA target may give the same advantage. The same principle applies, mutatis mutandis, to WAP genomic sequences.

Isolation of Milk From Lactating Transgenic Animals

Obtaining milk from a transgenic animal according to the present invention is accomplished by conventional means. See, for example, McBurney et al., *J. Lab. Clin. Med.* 64: 485 (1964); Velander et al., *Proc. Nat'l Acad. Sci. USA* 89: 12003 (1992), the respective contents of which are incorporated by reference. Fibrinogen or subunit chains or protein products thereof can be isolated and purified from milk or urine by conventional means without deleteriously affecting activity. A highly preferred method entails a combination of anion exchange and immunochromatographies, cryoprecipitations, and zinc ion-induced precipitation of either whole milk or milk whey (defatted milk) proteins. For these techniques, see Bringe et al., *J. Dairy Res.* 56:543 (1989), the contents of which is incorporated herein by reference.

Milk is known to contain a number of proteases that have the potential to degrade foreign proteins. These include in the main an alkaline protease with tryptic and chymotryptic activities, a serine protease, a chymotrypsin-like enzyme, an aminopeptidase and an acid protease. Clark et al. (1987), supra. It may be desirable, therefore, to protect newly secreted FIB or subunit chains thereof against proteolytic degradation. Such precautions include rapid processing of the milk after collection and addition to the milk of well known inhibitors of proteolysis, such as are listed in SIGMA CHEMICAL CO. CATALOG, 1993 edition, at page 850.

Detection and Ouantification of Transgenic FIB

The present inventors have used two sandwich ELISA formats to detect and quantify FIB in milk whey. One technique is a polyclonal antibody capture/FIB/monoclonal antibody detection system ("P/M") and the other which uses polyclonal antibodies both for capture and for detection ("P/P"). Both methods are described below. The P/M system benefits from greater specificity for hFIB as it recognizes only one epitope of about 6 to 20 amino acids in length specific to hFIB. However, because the P/M system recognizes only a single epitope, detection sensitivity is reduced. In contrast, the P/P system will provide less specificity as it recognizes many epitopes, but at the same time will provide greater detection sensitivity. As these multiple epitopes include epitopes conserved between mouse and human FIB, the background "FIB" signal is increased when measuring rhFIB in mouse milk by the P/P system. Detailed sandwich ELISA procedures are provided in EXAMPLE 7 below.

Purification and Biological Activity of Secreted Recombinant Fibrinogen

Mammalian proteins associated with hemostasis are well-conserved with respect to structure and function and thus it is necessary to both identify and purify rFIB from host body fluids. To establish that the FIB secreted in the milk of trigenic animals is indeed authentic, i.e, physiologically active, heterologous FIB, a number of well known, standard techniques may be carried out; these are listed below:

Physical Techniques (1) Physical separation and identification. A sequence of ion exchange chromatography and $Zn^{2+}$ selective precipitation achieves two main goals: the reduction of background protein (i.e., host FIB) from milk and an efficient isolation of rhFIB away from contaminating host FIB. Host FIB is present to a very small extent from natural passover of serum proteins into milk, but it is predominately due to injury of the mammary tissue from the milk collection process. Over half of the background milk proteins can be removed by anion exchange chromatography. Over 75% of the casein will be removed by the $Zn^{2+}$ selective precipitation process. The resulting rhFIB will be about 20–30% pure at this stage with an overall yield of about 50%. Control host milk whey serves as a negative human FIB control, and control whey doped with authentic human FIB serves as a positive control for human FIB. Transgenic whey serves as the source of recombinant FIB. The non-doped control whey contains host FIB that primarily partitions into a second 24 mm $Zn^{2+}$ supernatant fluid. Only about 1–3% of the FIB present in the final purified human or rhFIB samples will be host FIB. Thus, the $Zn^{2+}$ selective procedure enables an efficient separation of rhFIB from host FIB.

(2) Silver staining of SDS-PAGE gels of isolated rhFIB.

(3) Western blot analyses of isolated rhFIB.

(4) Fibrinopeptide A detection by EIA in thrombin-treated samples.

Biochemical Tests (5) Using ELISA signals (using detection by polyclonal anti-human fibrinogen antisera found in the supernatants after centrifugation to remove precipitates and/or clots) to track the consumption of isolated rhFIB by human thrombin.

(6) Determination of the apparent molecular weights of the assembled FIB molecule and of the separate α,β, and γ chains found under reducing conditions.

(7) The formation of a fibrin-like clot after treatment of the isolated rhFIB with human thrombin.

(8) The formation of α,β, and γ fibrin chains in these same clots.

(9) The release of fibrinopeptide A to confirm biological activity of isolated rhFIB by conversion to fibrin upon reaction with human thrombin.

For sources of these well-known techniques see, for example, Hartwig et al., *J. Biol. Chem.*, 266: 6578 (1991); Koopman et al., *J. Biol. Chem.*, 266: 13456 (1991); Lonnerdal et al., *J. Appl. Biochem.*, 4: 203 (1982); Farrell et al., *Biochem.*, 30: 9414 (1991); Goding, MONOCLONAL ANTIBODIES: PRINCIPLES AND PRACTICE, Academic Press, NY; Bolyard et al., *Gene* 66: 183 (1988); Hartwig et al., *J. Biol. Chem.*, 266: 6578 (1991); Roy et al., loc. cit., 266: 4758 (1991); Dempfie et al., *Thrombosis Res.*, 46: 19 (1987); Dempfie et al., loc. cit., 48: 223 (1987); and Yu et al., *Biochem. Biophys. Res. Commun.*, 96: 1032 (1980), the respective contents of which are incorporated by reference.

The present invention is further described by reference to the following illustrative examples.

EXAMPLE 1

WAP-Fibrinogen cDNA Constructs For Expression of Fibrinogen in Transgenic Animals Construction of Cassette Vectors FIB subunit chain DNAs, tissue-specific promoters, and secretion signal sequences were obtained from sources described above. FIB subunit chain cDNAs were cloned into a modified pUC 18 vector, and grown up in *E. coli* JM109. A pUC18 vector (GIBCO-BRL, Gaithersburg, Md.) was digested with HindIII+EcORI restriction endonucleases, blunted with T4 DNA polymerase in the presence of 100 mM dNTPs, and a Not I linker was ligated into the former HindIII-EcORI multiple cloning site. This modified pUC fragment was additionally digested with Not I+enzyme to remove extra (multiple copies) NotI linker sequences arising from ligation, and then religated and grown up in *E. coli* JM 109. This procedure modified the pUC18 vector by removing the entire multiple cloning region of pUC18 (including the Kpn I site) and replacing it with a Not I restriction site. The new vector was designated pUCNot1+.

Figure 2:
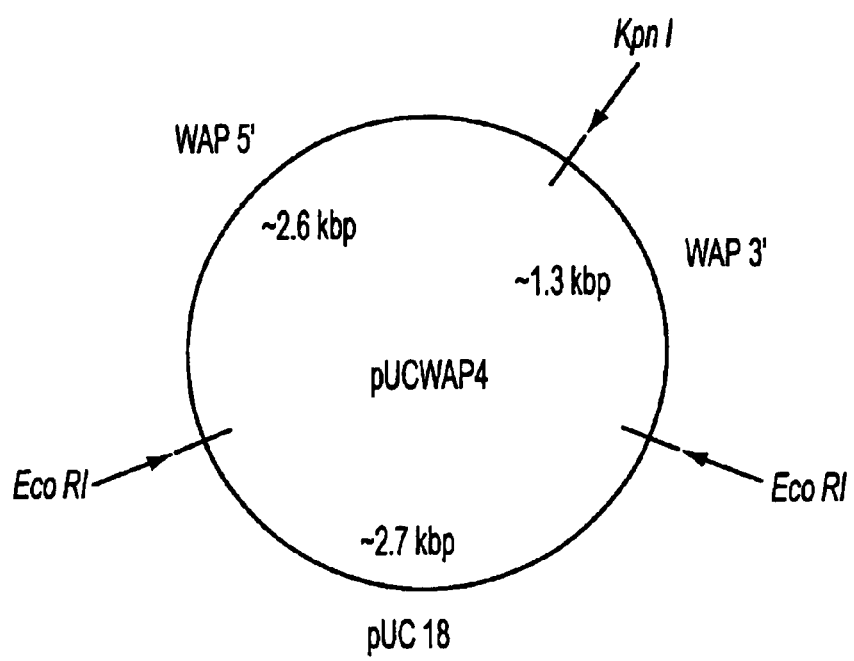
FIG. 2 is a sketch of the plasmid pUCWAP4 cassette vector containing ~2.6 kbp of WAP 5' promotor region, ~1.3 kbp of WAP 3' UTR and flanking 3' region.
Figure 3:
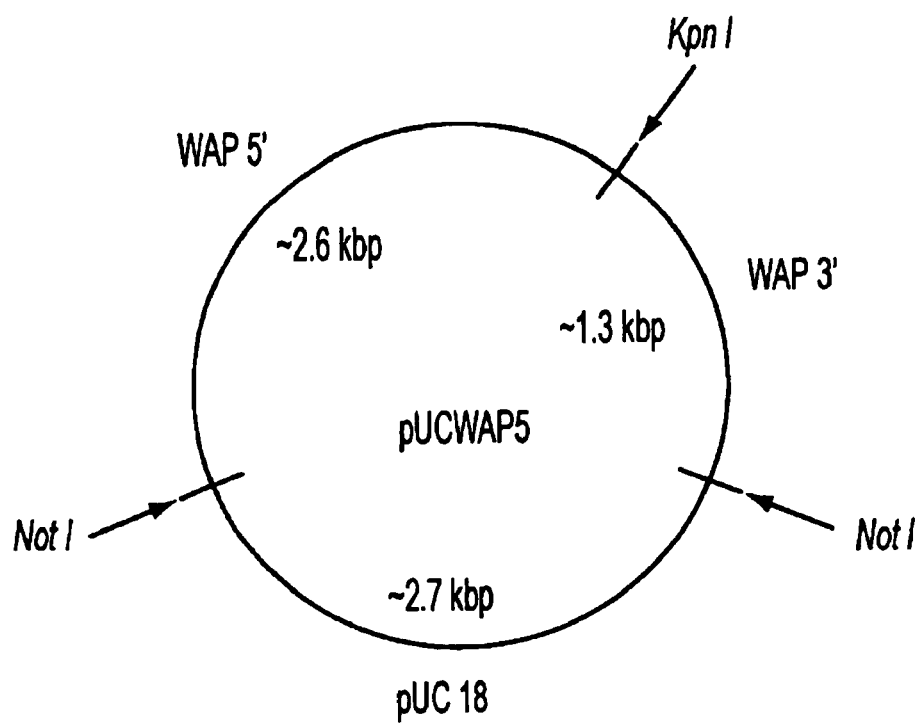
FIG. 3 is a sketch of the plasmid pUCWAP5 cassette vector containing the WAP fragment of pUCWAP4 with added Not I linkers.

A pUC vector containing ~2.6 kbp of WAP 5' promoter region, ~1.3 kbp of WAP 3' UTR and flanking 3', but no WAP coding or intronic regions was constructed (designated cassette vector pUCWAP4, FIG. 2; see WAP gene, FIG. 1, and cassette vector pUCWAP5, FIG. 3). The entire murine WAP gene including 2.6 kb of 5' untranslated sequence and 3' untranslated region may be obtained from Dr. I. Hennighausen, National Institutes of Health, Bethesda, Md. See, Campbell et al., *Nucleic Acids Res.*, 12:8685 (1984). The WAP fragment contained within the WAP4 vector contains a ~2.6 kbp WAP promoter 5' region beginning at EcORI#1 and ending at the translational start site of WAP which is immediately downstream of the unique Kpn I endonuclease restriction site (see FIG. 1). To this KpnI site was ligated a fragment of ~1.3 kbp of WAP UTR and flanking 3' sequence. This WAP 3' DNA included the region from immediately downstream of the WAP stop codon down to the EcOR1 #2 site. The WAP fragment contained in WAP4 was excised from the pUC vector using EcORI, and then blunted, and NotI linkers were added, further trimmed by NotI digestion, and ligated into the pUCNotI+ plasmid which had been linearized with NotI restriction endonuclease. The resulting plasmid was designated pUCWAP5 (see FIG. 3).

Amplification by PCR of Fibrinogen Subunit Chain cDNAs

Each of the cDNAs for Aα, Bβ, and Gγ chains for human fibrinogen were individually modified and amplified by polymerase chain reaction (PCR) to create KpnI endonuclease restriction sites on their 5' and 3' ends. The 5' KpnI site was engineered by PCR using the primers [containing the 6 base sequence (GGTACC shown underlined in Table 1)] that immediately flanks the ATG start codon in the cDNAs of Aα, Bβ, and Gγ chains for hFIB. After amplification, the ends of the extension using PCR products were blunted by T4-polymerase (in the presence of deoxynucleosidetriphosphates to inhibit processive exonuclease activity. In a similar fashion, a KpnI site was engineered by site modification into the 6 base sequence GGTACC shown underlined in Table 1 immediately flanking the stop sequence in the 3' UTR of each cDNA for Aα, Bβ, and Gγ chains for hFIB. The complement of the stop sequences is shown in bold in the 3' primers in Table 1.

TABLE 1

Oligonucleotides for Amplifying FIB Subunit Chain cDNA

| | | |
|---|---|---|
| Aα 5' | GCTA<u>GGTACC</u>ATGTTTTCCATGAGGATCGT | Seq. ID No. 3 |
| Aα 3' | CAGT<u>GGTACC</u>CTAGACAGGGCGAGATTTAG | Seq. ID No. 4 |
| Bβ 5' | GCTA<u>GGTACC</u>ATGAAAAGAATGGTTTCGTG | Seq. ID No. 5 |
| Bβ 3' | CAGT<u>GGTACC</u>CTATTGCTGTGGGAAGAAGG | Seq. ID No. 6 |
| Gγ 5' | GCTA<u>GGTACC</u>ATGAGTTGGTCCTTGCACCC | Seq. ID No. 7 |
| Gγ 3' | CAGT<u>GGTACC</u>TTAAACGTCTCCAGCCTGTT | Seq. ID No. 8 |

GGTACC = KpnI site
ATG = start codon
CTA and TTA = stop codon

Construction of pUC Plasmids Containing Fibrinogen Subunit Chain cDNA

Figure 4:
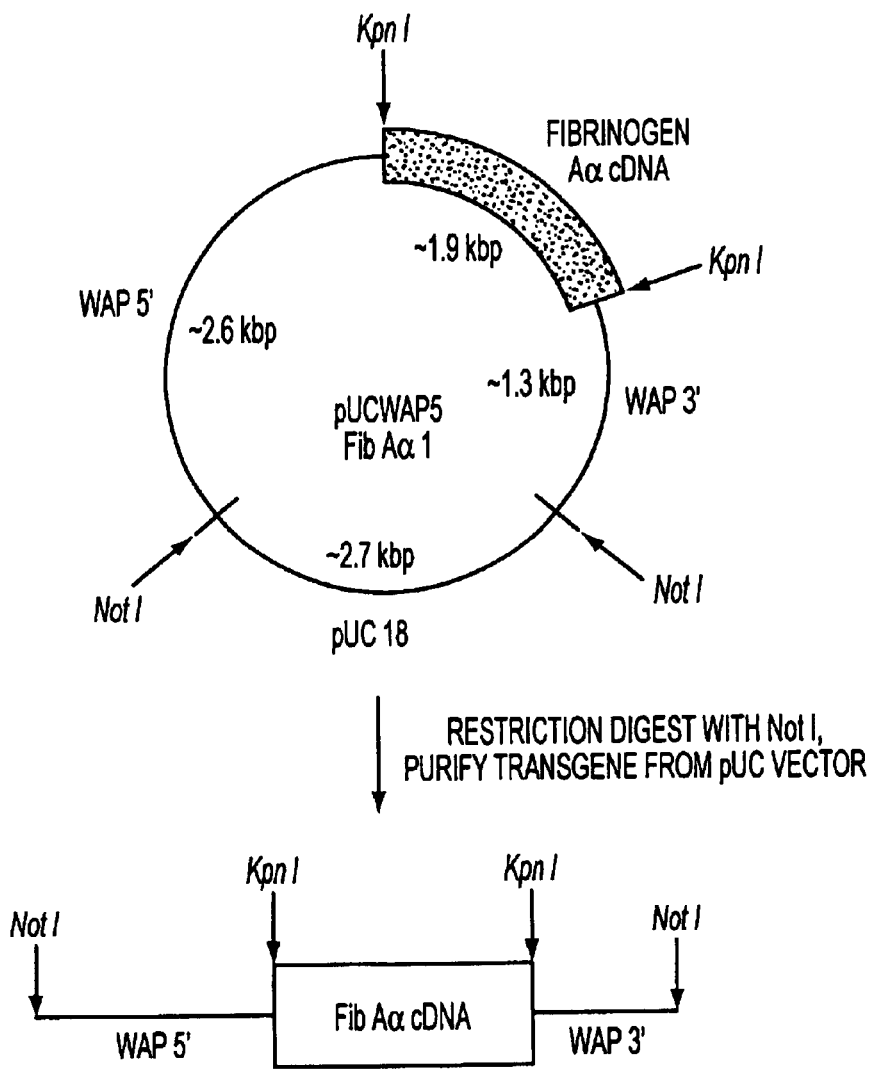
FIG. 4 is a sketch of the pUCWAP5 plasmid incorporating a polynucleotide encoding the FIB Aα 1 chain.
Figure 5:
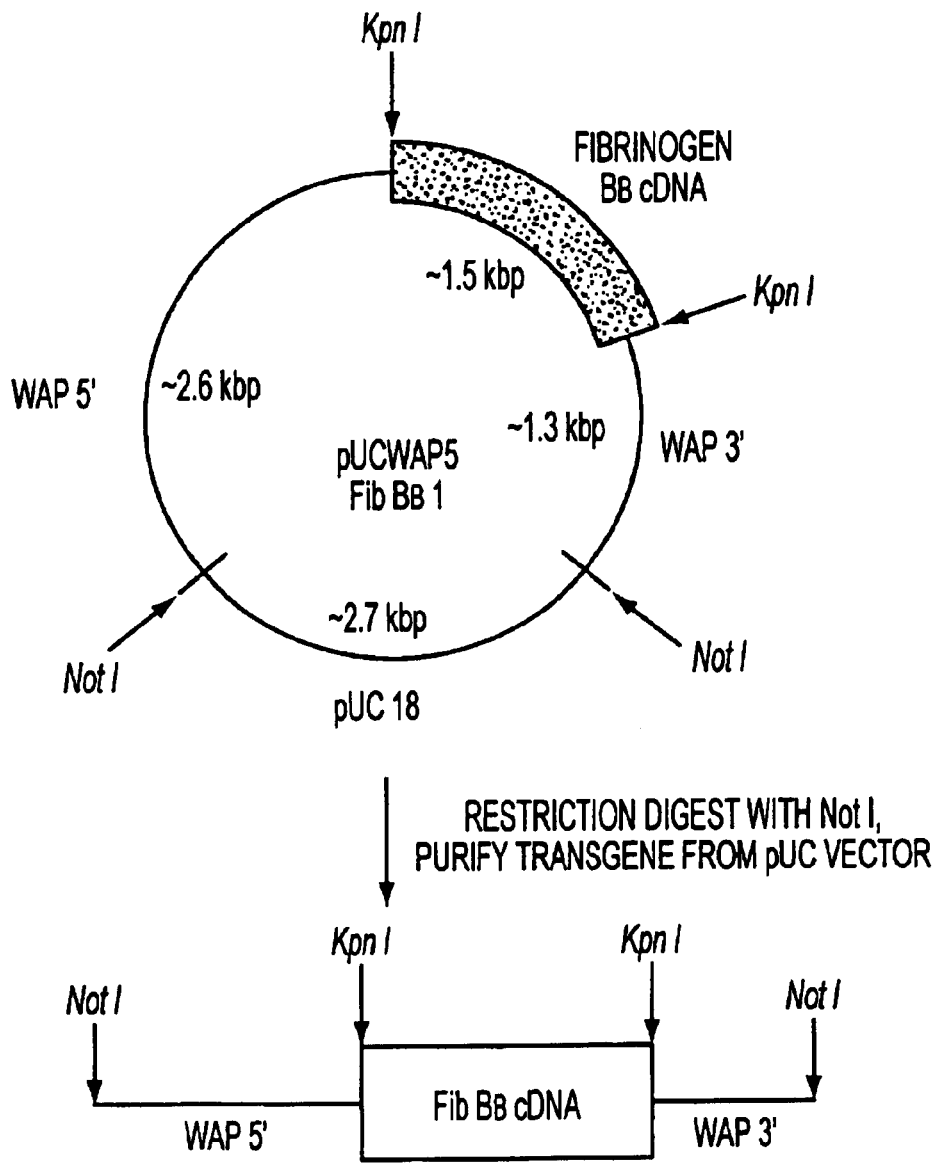
FIG. 5 is a sketch of the pUCWAP5 plasmid incorporating a polynucleotide encoding the FIB Bβ 1 chain.
Figure 6:
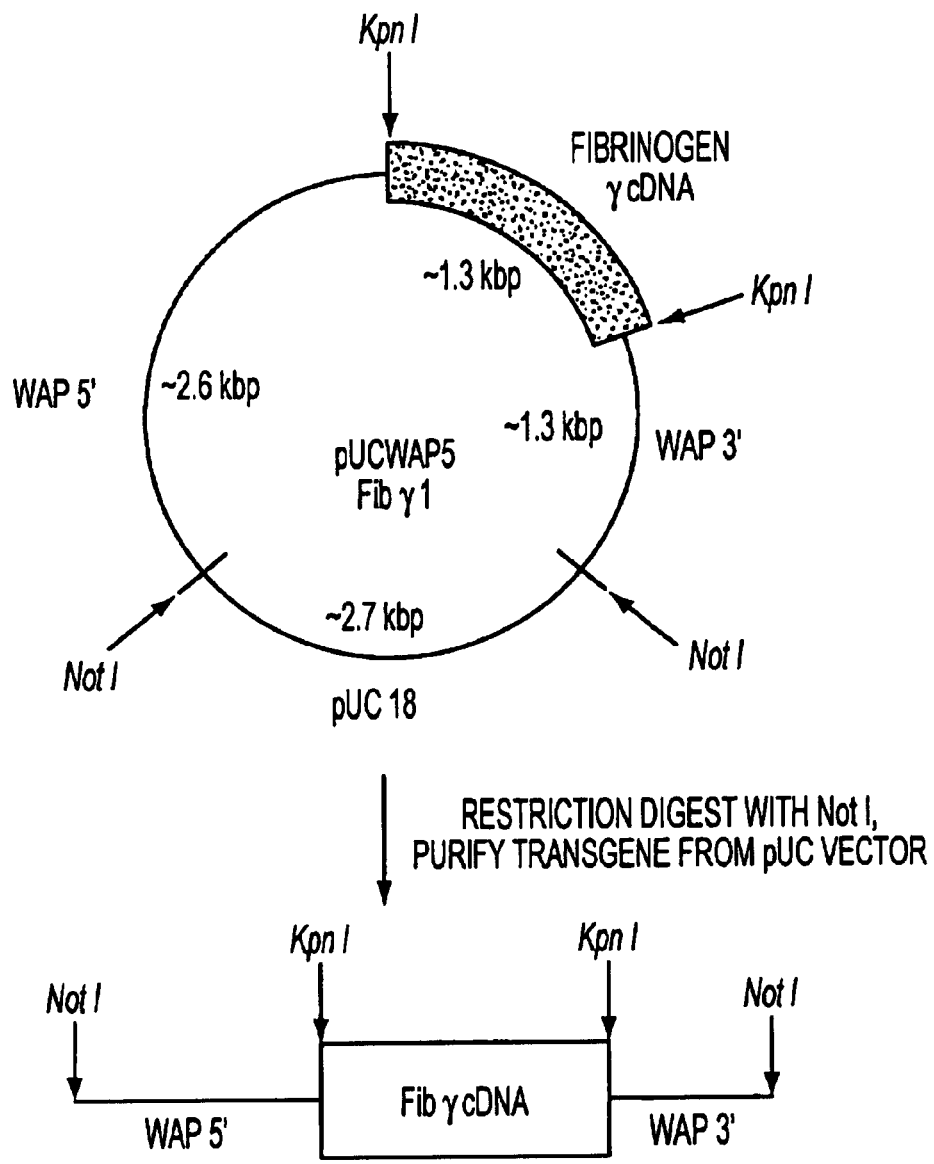
FIG. 6 is a sketch of the pUCWAP5 plasmid incorporating a polynucleotide encoding the FIB Gγ 1 chain.

The blunted PCR products of the cDNAs for the Bβ and Gγ chains of human fibrinogen were digested with KpnI restriction endonuclease. In the case of the Aα chain, the PCR product was blunt-end cloned into pUCNotI+ (which had been digested with NotI and blunted with T4 Polymerase) prior to partial KpnI digestion. This intermediate cloning and partial digestion step was necessary to generate intact coding fragment due to the presence of an internal KpnI site within the Aα chain cDNA. The intact Aα chain cDNA fragment was selected by gel electrophoresis, and cloned into the KpnI site at the junction between the WAP 5' promoter and WAP 3' UTR/flanking sequences within the pUCWAP5 plasmid. The KpnI-digested PCR products from Bβ and Gγ chains for human fibrinogen were each directly cloned into a pUCWAP5 plasmid at the KpnI site. Separate electroporation transformation reactions were done on *E. coli* using each of the three pUCWAP5/fibrinogen cDNA preparations, and colonies were picked and grown up in TB ampicillin broth. Plasmid preparations from these colonies were analyzed by restriction enzyme digestion and gel electrophoresis. The correct size and orientations were selected and one clone for each WAP-fibrinogen cDNA construct was sequenced at the WAP promoter 5':fibrinogen cDNA and fibrinogen cDNA:WAP 3' UTR and flanking junctions. Schematics summarizing the construction of the WAP-Aα (about 5.8 kbp), -Bβ (about 5.4 kbp), and -Gγ (about 5.2 kbp) cDNA plasmid and linearized transgenes for human fibrinogen are given in FIGS. 4, 5, and 6, respectively.

EXAMPLE 2

Preparation of DNAs for Microinjection

The intact and linearized WAP 5' promoter/fibrinogen cDNA/WAP 3' UTR and flanking fragments were excised from each pUCWAP5 plasmids by NotI restriction endonuclease digestion and purified by low melting point agarose electrophoresis. The DNA:agarose band was cut from the gel slab. The agarose band was then treated with agarase to degrade and remove agarose contamination.

After digestion, the solution containing the cDNA was brought to 10 mM Mg2+, 20 mM EDTA and 0.1% SDS and then extracted with phenol/chloroform. DNA was precipitated from the aqueous layer with 2.5 volumes of ethanol in the presence of 0.3 M sodium acetate at −20° C. overnight. After centrifugation, the pellet was washed with 70% ethanol, dried, and each of the constructs was resuspended and dissolved in Brinster microinjection buffer to a total (α, β, plus γ) concentration of about 1.2 to 5 μg/ml. Brinster et al., *Proc Natl. Acad. Sci. USA* 82:4438 (1985), incorporated by reference.

EXAMPLE 3

Transgenic Mice

Transgenic mice were produced essentially as described by Hogan et al., *Manipulating The Mouse Embryo*, Cold Spring Harbor Press, 1986, incorporated by reference. The procedures employed are outlined below.

Glass needles for micro-injection were prepared using a micropipet puller and microforge. Injections were performed using a Nikon microscope having Hoffman Modulation Contrast optics, with Narashigi micromanipulators and a pico-injector driven by $N_2$ (Narashigi).

Fertilized mouse embryos were surgically removed from the oviducts of superovulated female CD-1 mice and placed into M2 medium. Cumulus cells were removed from the embryos with hyaluronidase at 300 μg/ml. The embryos were then rinsed in new M2 medium, and transferred into M16 medium for storage at 37° C. prior to injection.

Stock solutions containing about 1.2 μg/ml (having about 0.4 μg/ml each of the linearized constructs containing the Aα, Bβ, and Gγ chains cDNAs for human fibrinogen, or about 60–70 copies/pl of each construct) were prepared and microinjected into the pronuclei of 1 cell mouse embryos. In addition, stock solutions containing about 5 μg/ml total DNA (having about 1.7 μg/ml of linearized constructs containing each of the Aα, Bβ, and Gγ chains cDNAs for human fibrinogen or about 200 copies/pl of each construct) were prepared and microinjected into the pronuclei of 1 cell mouse embryos.

After injecting the DNA solution into the male pronucleus, embryos were implanted into avertin-anesthetized CD-1 recipient females made pseudo-pregnant by mating with vasectomized males. About 25–30 microinjected mouse embryos per recipient were transferred into pseudopregnant females. Embryos were allowed to come to term and the newborn mice were analyzed for the presence of the transgene by PCR using murine WAP and a FIB-specific primer as described below.

Table 2 summarizes the embryo transfer data from an experiment that produced transgenic fibrinogen-producing mice. Separate PCR analysis for detection of each of the cDNAs of fibrinogen was done on DNA purified from biopsied tail tissues by the method shown in Example 4 below. The oligonucleotide primers shown in Table 3 were used to detect each of the FIB cDNAs. Detection of each chain required a WAP oligonucleotide (no. 1 in Table 3) and one of the other oligonucleotides (Nos. 2, 3 or 4).

Table 2

Transfers of Fibrinogen Constructs

Thirty transfers with the FIB constructs were performed. The three subunit chain constructs were co-injected at total DNA concentrations of 1.2 μg/ml and 5 μg/ml or 200 total copies/pl and 800 total copies/pl, respectively. Fourteen transfers were made with 1.2 μg/ml-injected embryos and sixteen with 5 μg/ml-inject embryos. Eighteen Founder ("Fo") animals were produced that carried at least one construct. Eight Fo mice were mated with control mice which resulted in five lines transmitting the transgene. First generation offspring ("F1") from lines 1,23 and 85 have been bred and litters produced.

TABLE 2

Transfers of Fibrinogen Constructs
Thirty transfers with the FIB constructs were
performed. The three subunit chain constructs were co-
injected at total DNA concentrations of 1.2 μg/ml and 5 μg/ml
or 200 total copies/pl and 800 total copies/pl,
respectively. Fourteen transfers were made with 1.2 μg/ml-
injected embryos and sixteen with 5 μg/ml-inject
embryos. Eighteen Founder ("Fo") animals were produced
that carried at least one construct. Eight Fo mice were
mated with control mice which resulted in five lines
transmitting the transgene. First generation offspring
("F1") from lines 1, 23 and 85 have been bred and litters
produced.

|  | 1.2 μg/ml | 5 μg/ml |
| --- | --- | --- |
| Transfers: | 14 | 16 |
| Pups alive: | 68 | 69 |
| Embryos injected: | 696 | 1098 |
| Embryos transferred: | 480 | 675 |
| Embryos per transferred: | 34.2 | 42.1 |
| Pups per litter | 6.2 | 5.3 |
| Transfers pregnant: | 11 | 13 |

TABLE 2-continued

Transfers of Fibrinogen Constructs
Thirty transfers with the FIB constructs were
performed. The three subunit chain constructs were co-
injected at total DNA concentrations of 1.2 μg/ml and 5 μg/ml
or 200 total copies/pl and 800 total copies/pl,
respectively. Fourteen transfers were made with 1.2 μg/ml-
injected embryos and sixteen with 5 μg/ml-inject
embryos. Eighteen Founder ("Fo") animals were produced
that carried at least one construct. Eight Fo mice were
mated with control mice which resulted in five lines
transmitting the transgene. First generation offspring
("F1") from lines 1, 23 and 85 have been bred and litters
produced.

|  | 1.2 μg/ml | 5 μg/ml |
|---|---|---|
| Pregnancy rate: | 78% | 81% |
| Mice tested: | 68 | 69 |
| Number transgenic: | 7 | 11 |
| Percent transgenic: | 10% | 15% |
| % Positive for α, β, γ: | 85% | 72% |
| α, β, γ Transgenic females: | 3 | 3 |

TABLE 3

Oligonucleotide Primers Used for PCR Detection of Human
Fibrinogen Transgenic Mouse Seq. ID No. 9. Sense strand. WAP-specific oligonucleotides.
5'-CTGTGTGGCCAAGAAGGAAGTGTTG-3'
Seq. ID No. 10. Antisense oligonucleotide. Aα chain detection.
5'-GATGTCTTTCCACAACCCTTGGGC-3'
Seq. ID No. 11. Antisense oligonucleotide. Bβ chain detection.
5'-CCCGATAGCCACCTCCTCTGATG-3'
Seq. ID No. 12. Antisense oligonucleotide. Gγ chain detection.
5'-CCTGGACTTCAAAGTAGCAGCGTC-3'

A summary of the types of fibrinogen transgenic mice detected in founder and offspring of founder mice is given in Table 4. A listing of the positive FIB triple construct founders (Fo) and a listing of β-chain positive transgenic mice are also given in Table 4.

TABLE 4

Transmission of Fibrinogen Transgenes

| Mouse No. | Transmission Frequency | Genes Transmitted |
|---|---|---|
| 1 (α, β, γ) | 9/13 (69%) | α, β, γ |
| 23 (α, β, γ) | 6/12 (50%) | α, β, γ (3/6); β only (3/6) |
| 109 (α, β, γ) | 5/11 (45%) | α, β, γ |
| 112 (α, β, γ) | 5/8 (62%) | α, β, γ (4/6); α only (1/6); α, γ only (1/6) |
| 85 (α, β) | 1/6 (16%) | β only |
| 113 (αβγ) | 0/8 | None |
| 89 (α) | 0/6 | None |

Positive Fibrinogen Triple Construct F1's
1-2,1-5,1-6,1-11,1-12,1-14,1-16,1-17,1-20,23-3,23-4,23-12,
109-3,109-4,109-5,109-10,109-11,112-3,112-6,112-7,112-8

β-Chain Positive Mice
23-2,23-7,23-11,85-2

All embryos were injected with the three FIB constructs at a total DNA concentration of 5 μg/ml or about 200–300 copies of each construct per pl.

Figure 7:
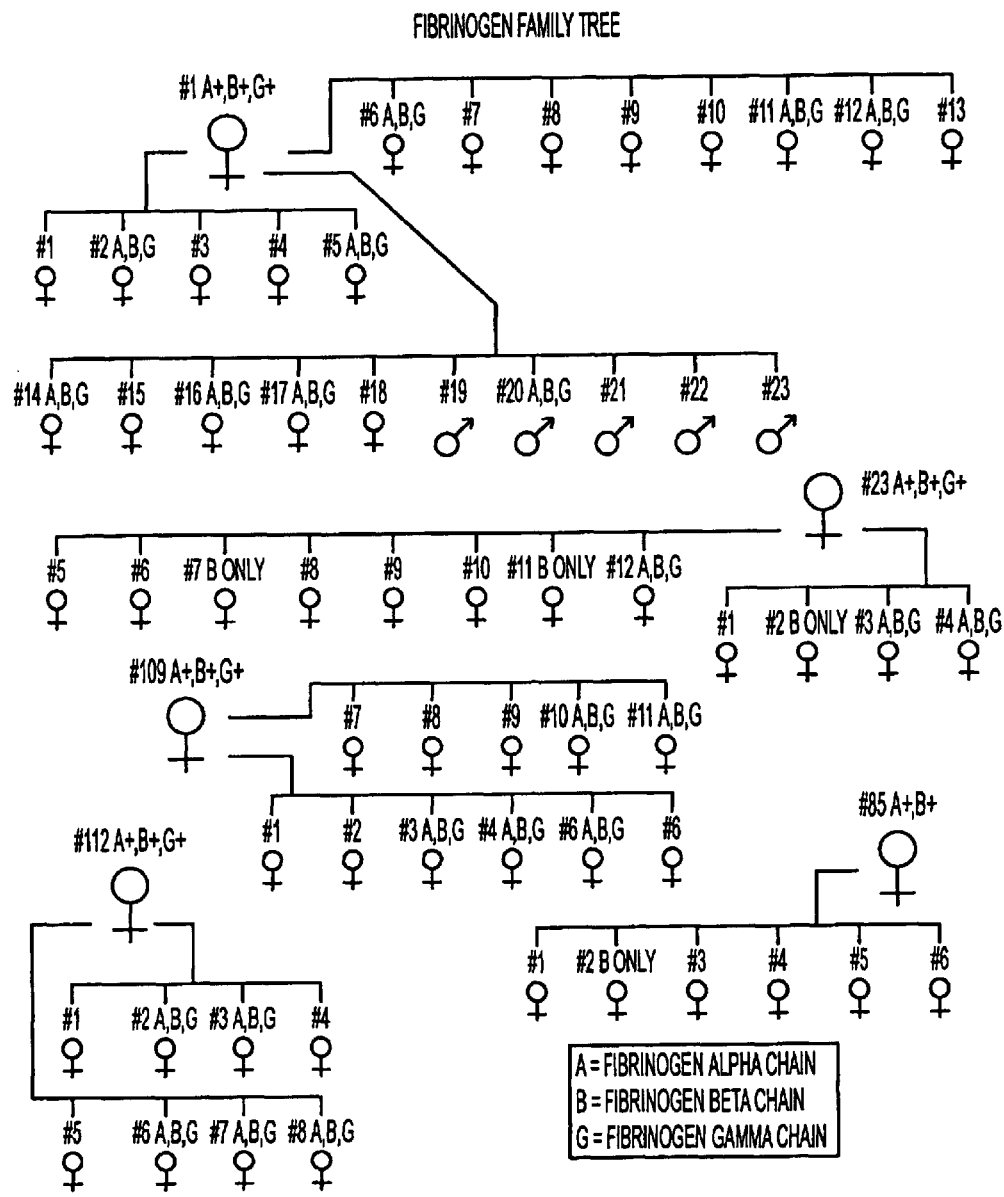
FIG. 7 shows the family tree of transgenic mice that have incorporated into their genome DNAs encoding FIB genes.

A family tree of transgene passage from Fo to F1 females is shown FIG. 7. Males were not retained.

EXAMPLE 4

Transgenic Animal DNA

DNA can be prepared from tissue of a transgenic animal of any species by the method exemplified below for mice. Marmur, *J. Mol. Biol.* 3:208 (1961), incorporated by reference.

A 5 mm piece of mouse tail was removed from young, potentially transgenic mice at weaning (3 weeks) age, and frozen in liquid nitrogen. To the frozen tissue was added 840 μl of Lysing Solution (8 mM EDTA-0.8% SDS-0.8% 2-mercaptoethanol-80 μg/ml Proteinase K-1 M sodium chlorate in 40 mM TRIS buffer pH 8.0 and 120 mM NaCl, and the mixture incubated at 50° C. The mixture was then extracted with 250 μl of phenol/chloroform/isoamyl alcohol (25:24:1) for 10–15 seconds, then centrifuged for 10 minutes. The supernatant fluid (about 830 μl) was removed to a fresh tube, and a DNA clot produced by vortexing the solution with 0.6 vols. of isopropanol. The mother liquor was decanted, and the DNA clot rinsed twice with 80% ethanol. The DNA clot was isolated by 5 minutes of centrifugation, aspiration of the supernatant fluid, and air drying of the clot with a stream of air for 10 minutes.

The DNA clot was dissolved in 250 μl of TE buffer (10 mM Tris.HCl, pH 7.0–1 mM EDTA, and the solution treated with 10 μl of a RNase mixture (1 mg/ml RNAse A and 4,000 units/ml RNAse T1) for 1 h at 37° C. This mixture was shaken with 50 μl of a 24:1 (v/v) solution of chloroform-isoamyl alcohol for 5–10 secs., centrifuged, and the supernatant fluid transferred to a fresh tube.

The recovered supernatant fluid above was mixed sequentially with 25 μl of 3 M sodium acetate and 0.5 ml of 95% ethanol. The supernatant fluid was decanted from the precipitated DNA, and the precipitate washed with 80% ethanol. The purified DNA was isolated by centrifugation, air dried, then dissolved in 150 μl of TE.

Essentially the same technique was used to prepare DNA from pigs, and the same or similar techniques can be used to prepare DNA from other animals.

PCR reactions on DNA samples isolated from transgenic animal tissue samples were carried out conventionally, as described above. Concentrations of DNA isolates were determined by measuring the absorbency at 260 nm of 1:20 dilutions of the TE solutions described above. A portion of the sample was then diluted into 100 μl of TE to a concentration of 30 ng/μl.

PCR Reaction Mixtures (20 μl volume)

| Component | Volume (μl) | Concentration |
|---|---|---|
| HOH | 13.25 | — |
| 10X Taq buffer | 2.5 | 1 |
| dNTPs | 2.0 | 0.2 mM |
| $MgCl_2$ | 1.5 | 1.5 mM |
| Primer 1 | 0.3125 | 0.5 μM |
| Primer 2 | 0.3125 | 0.5 μM |
| Taq polymerase | 0.125 | 25 μunits/μl |
| DNA template | 1.0 | 1.2 ng/μl |

Procedure

Embryo lysing buffer (5 μl, 0.9% Nonidet P-40 and 0.9% Tween 20 in 20 mM TRIS buffer) was added to each PCR tube along with 1 μl of prepared DNA solution, and the mixture overlaid with 25 μl of mineral oil. The tubes were placed in an automatic temperature cycler (such as that manufactured by N.J. Research) and heated to 98° C. for 2 minutes; the temperature was then brought down to 85° C.

PCR reaction mixture (20 μl) was added to each tube and 40 cycles of the following protocol carried out:

Denaturation at 96° C. for 20 seconds

Annealing at 55° C. for 1 minute

Elongation at 75° C. for 30 seconds

PCR reaction products were analyzed by running 20% of the reaction mixture products on agarose gels and identifying fragment sizes by comparison with marker DNA fragments.

FIG. 7 shows that a variety of founder animals having A+ and/or B+ and/or G+constructs can transmit all three or some of the A+, B+, and G+transgenes. All animals were produced from embryos having coinjections of the same DNA solution containing all of the A+, B+, and G+ constructs. Detection of A+, B+ and G+ DNAs was done by PCR as described above. Founder animals 1, 23, 109 and 112 had all three transgenes. Founder animal 85 had only A+ and B+. These founder animals were outbred with control (nontransgenic) mice. Animals 1 and 109 passed all three transgenes to 5 of 13 and 5 of 11 offspring, respectively, which is typical of Mendelian genomic transmission for a single allele. Founder animals 23 and 112 transmitted some transgene to 6 of 12 and 7 of 8 animals, respectively. Several offspring of animal 23 had only B+, while one offspring of animal 112 had only A+ and another had A+ and G+. Thus, founder animals 23 and 112 are examples of triple transgenic animals having a confirmed separate B+allele in the case of animal 23 and having a separate A+ and B+allele in the case of animal 112. Founder animal 85 is also an example of a mouse with a B+ only allele. Thus, crossbreeding of animals having separate alleles and therefore loci for each gene can be done in order to increase expression (the control over a rate limited B+ chain may be overcome by having a B+ allele with a more inducible loci). Furthermore, double and triple heterozygotes of the same gene (either A+ and/or B+ and/or G+) can be achieved to boost production levels (i.e., produce a A+B+G+, B+ animal by crossbreeding a B+ animal, and further crossbreeding that A+B+G+,B+ animal with a different B+ line to obtain A+B+G+,B+B+).

EXAMPLE 5

Transgenic Pigs

Embryos were recovered from the oviduct. They were placed into a 1.5 ml microfuge tube containing approximately 0.5 ml embryo transfer media (phosphate buffered saline+10% fetal calf serum, Gibco BRL). These were then centrifuged for 12 minutes at 16,000×g RCF (13,450 RPM) in a microcentrifuge (Allied Instruments, model 235C). Embryos were removed from the microfuge tube with a drawn and polished Pasteur pipette and placed into a 35 mm petri dish for examination. If the cytoplasm was still opaque with lipid such that pronuclei were not visible, the embryos were centrifuged again for 15 minutes. Embryos to be microinjected were placed into a microdrop of media (approximately 100 μl) in the center of the lid of a 100 mm petri dish. Silicone oil was used to cover the microdrop and fill the lid to prevent media from evaporating. The petri dish lid containing the embryos was set onto an inverted microscope (Carl Zeiss) equipped with both a heated stage and Hoffman Modulation Contrast optics (200×final magnification). A finely drawn (Kopf Vertical Pipette Puller, model 720) and polished (Narishige microforge, model MF-35) micropipette was used to stabilize the embryos while about 1–2 picoliters of HPLC-purified DNA solution containing approximately 200–500 copies of DNA construct was delivered into the male pronucleus with another finely drawn micropipette. Embryos surviving the microinjection process as judged by morphological observation were loaded into a polypropylene tube (2 mm ID) for transfer into the recipient pig. Seven surgical transfers of pig embryos were made. These embryos had been coinjected with the WAP-fibrinogen cDNA constructs used in the above mentioned transgenic fibrinogen mice Only one of these recipient gilts was confirmed pregnant by ultrasound. The (apparent) non-pregnant animals were kept to tentative term as their (potential) litter sizes may have been too small to detect by ultrasound analysis (In the past, three litters of four piglets or fewer were not detected by ultrasound. Some of these litters produced transgenic animals.)

TABLE 5

Fibrinogen Porcine Embryo Data

|  | Expt. 1 | Expt. 2 | Transfer Totals Oct. 25, 1993 | ID |
|---|---|---|---|---|
| Number of donors: | 8 | 8 | Transfer #1 50 | embryos #129 |
| Number of ovulations: | 261 | 283 | Transfer #2 47 | embryos #147 |
| Embryos collected: | 250 | 296 | Transfer #3 44 | embryos #108 |
| Number of UFO's: | 99 | 77 |  |  |
| UFO's that cleaved: | 29 | 6 |  |  |
| Number injected: | 141 | 219 | October 28 |  |
| Number transferred: | 141 | 200 | Transfer #1 50 | embryos #114 |
| Transfers: | 3 | 4 | Transfer #2 50 | embryos #139 |
| Embryos/Transfer: | 47 | 50 | Transfer #3 50 | embryos #140 |
| Ovulations/Pig: | 32.6 | 35.3 | Transfer #4 50 | embryos #131 |
| Embryos/Pig: | 31.2 | 37 |  |  |

All embryos were injected with the three fibrinogen constructs at a total DNA concentration of 5 μg/ml or about 200–300 copies of each construct per pl.

EXAMPLE 6

Preparation of Milk and Whey from Transgenic Animals

Lactating mice were milked once on about day 12 of lactation. The mice were first separated from their young for approximately 5 hours. They were then anesthetized with 0.4 ml avertin at 2.5% (im.), and 0.2 ml oxytocin was then administered at 2.5 IU/ml (ip.) to permit release of the milk. A milking device consisting of a vacuum pump (2.5 psi) and syringe with an Eppendorf tip was used to direct milk into an eppendorf tube. As noted above, milk should not be placed on ice because of cryoprecipitation of fibrinogen.

To prepare whey, milk was diluted 1:1 with TRIS buffer (0.03 M Tris pH 7.4; 0.06 M NaCl) and centrifuged in a TLA-100 rotor in a Beckman TL-100 table top ultracentrifuge at 51,000 rpm (89,000×g) for 30 minutes at room temperature. After centrifugation, the whey (infranatant fluid) was collected with an 18 gauge needle, leaving the casein pellet and upper cream layer in the tube. To remove solids or cream that co-transferred during the initial recovery, the whey obtained from the first centrifugation was subjected to a second spin at 12,000 rpm for 30 minutes in a TMA-4 rotor in a Tomy MTX-150 centrifuge. Following the second spin, the whey was recovered as before.

EXAMPLE 7

Determination of Fibrinogen in Milk by a Sandwich ELISA

A sandwich ELISA was used to measure the amount of FIB protein produced by founder and progenic transgenic animals in the diluted skim or defatted milk (here termed "whey"); the whey value is used to estimate the concentration of FIB in whole milk.

Generally, in the first step of the P/M ELISA system, a fibrinogen or fibrinogen chain analyte-containing sample (for example, whey) is incubated with a mouse anti-human fibrinogen mAb (clonal number 311, American Diagnostics) that is reactive with the alpha chain of fibrinogen to form a mAb-fibrinogen (or chain) first complex. This first complex is then "captured" by incubation with rabbit polyclonal anti-human fibrinogen antibodies immobilized in microliter plate wells. In the detection step, the captured fibrinogen (or alpha chains) is contacted with labeled (horse radish peroxidase) anti-mouse IgG, and the amount of label quantified by reaction with o-phenylenediamine and measurement of absorbency at 490 nm; this is a measure of the amount of analyte present. Standard curves were obtained by spiking the whey of control (nontransgenic) animals with pure reference human FIB material. Thus, the presence of background amounts of FIB is normalized by the standard curve. This sandwich ELISA gives very low background values (about 0.06 absorbency units at 490 nm) for mouse whey alone with no human FIB. Note the typical signals given in Table 6 are about 0.25 or higher absorbency units at this wavelength.

In the P/P system, Immulon II 96-well microliter plates were coated with 100 μl/well of 1:500 diluted rabbit anti-human FIB (Celsus cat. no. 60960) in 0.1 M NaHCO$_3$-0.1 M NaCl, pH 9.6, for 24 hours at refrigerator temperatures. Coated wells were washed three times with Wash Buffer (25 mM Tris-HCl-50 mM NaCl-0.5% Tween-20, pH 7.0) and blocked for 20 minutes with Dilution Buffer (1 mg/ml PEG in 25 mM Tris-HCl-50 mM NaCl, pH 7.0) at room temperature. A volume of 100 Al of standard human FIB (100 ng/ml to 1.9 ng/ml range) and/or 100 Al of diluted milk sample was added to each well, and the mixtures incubated at 37° C. for 45 minutes. The wells were washed and blocked as above for 10 minutes at room temperature. 100 μl of 1:1000 diluted horse radish peroxide-conjugated rabbit anti-human FIB were added to each well, and the mixtures incubated at 37° C. for 45 minutes. After washing the wells as above, 100 μl of o-phenylenediamine solution (1 tablet/5 ml diluent) were added to each well. After waiting about 2–3 minutes for color development, reactions were stopped by the addition to each well of 100 μl of 3 N H$^2$SO$_4$. Plates were then read at 490 nm.

Table 6 presents the results of the analyses of rhFIB by the P/M ELISA system described above in the first lactation whey (and in whole milk by calculation) of three founder (Fo) transgenic mice whose genome contained each of the Aα, Bβ, and Gγ chains cDNAs for human fibrinogen. In this experiment, "whey" refers to skim milk diluted 1.7× with EDTA to solubilize the caseins. The averages of four dilutions of each whey sample for the three test animals was about 16.3, 3.86 and 7.55 μg/ml, respectively. The corresponding values for whole milk were 27.6, 6.56 and 12.8. Second lactation production of rhFIB was similar.

In another experiment with the same animals the first lactation whey fibrinogen concentrations averaged about 22±4 (animal 1), 9±2 (animal 22) and 11±3 (animal 23) μg/ml. The second lactation of animal 1 produced 17±3 μg/ml whey.

The P/M ELISA system was used to assay for rhFIB in the third lactation milk of mouse no. 1/Fo and the first lactation of mouse no. 1 female offspring (1-11/F1). As shown in the data of Table 7, mouse no. 1/Fo had about 71 μg/ml, and her offspring (no. 1-11/F1) had about 53 pg/ml total FIB signal. Thus, the amount of rFIB after subtracting background is calculated to be about 50 μg/ml for mouse no. 1/Fo and about 32 μg/ml for offspring 1-11/F1, respectively, over that of endogenous FIB present from serum to milk passover. The slightly lower value (28 μg/ml) of the P/M assay of the previous lactation of mouse no. 1/Fo is not significantly different than the P/P value when lower detection sensitivity of the former method is taken into account. It is noted that collection of mouse milk is inherently traumatic and leads to serum passover of endogenous mFIB.

In summary, mouse no. 1/Fo (founder) produced rFIB in milk at a level of about 30 μg/ml or greater over 3 lactations as detected by either the P/M or P/P ELISA methods, and has passed this trait on into the F1 generation which, in mouse no. 1-11/F1, produced 32 μg/ml rFIB.

TABLE 7

Inheritability of Transgenic rhFIB Gene

| Mouse No. | μg rhFIB/ml 5× diluted whey | μg rhFIB/ml milk |
|---|---|---|
| 1/Fo | 14.0 ± 2.0 | 71.0 |
| 1–11/F1 | 10.4 ± 0.8 | 53.0 |
| Control whey | 4.0 ± 0.7 | 21.0 |

These productions are substantially greater than the 2 μg/ml produced in the COS1 system described by Roy et al., 1991, above.

Western analysis of control mouse milk using polyclonal anti-human fibrinogen antibody showed about 21 μg/ml of background fibrinogen signal (see Table 7). Western analysis that uses the clonal number 311 or Y18 monoclonal antibody has a lower limit of sensitivity of about 1 μl sample of 100 μg/ml fibrinogen (Phastgel system) or 20 μl of 25 μg/ml in a 3" by 4" SDS-PAGE gel.

TABLE 6

| | A | B | C | D | E | WHEY | MILK |
|---|---|---|---|---|---|---|---|
| 1 | Animal | Dilutions | AVG ABS 490 nm | | FIB μg/ml | AVG FIB μg/ml | AVG FIB μg/ml |
| 2 | #1 DAY 6 | 100 | 0.623 | 0.132 | 13.2 | | |
| 3 | | 200 | 0.523 | 0.088 | 17.6 | 16.3 | 27.6 |
| 4 | | 400 | 0.434 | 0.049 | 19.4 | | |
| 5 | | 800 | 0.334 | 0.018 | 14.7 | | |
| 6 | | | | | | | |
| 7 | #22 | 100 | 0.374 | 0.022 | 2.16 | | |
| 8 | | 200 | 0.335 | 0.018 | 3.69 | 3.86 | 6.56 |
| 9 | | 400 | 0.273 | 0.014 | 5.73 | | |
| 10 | | 800 | 0.251 | 0.013 | 10.3 | | |
| 11 | | | | | | | |
| 12 | #23 | 100 | 0.477 | 0.067 | 6.75 | | |
| 13 | | 200 | 0.384 | 0.026 | 5.22 | 7.55 | 12.8 |
| 14 | | 400 | 0.338 | 0.019 | 7.44 | | |
| 15 | | 800 | 0.261 | 0.013 | 10.8 | | |

EXAMPLE 8

Confirmation That Transgenic Fibrinogen is Actually Recombinant Human Fibrinogen Materials Used to Analyze Fibrinogen Rabbit antisera against human fibrinogen was purchased from Celsus laboratories (Cincinnati, Ohio.). Rabbit antisera against human fibrinogen conjugated to horseradish peroxidase (HRP) was purchased from Dako corporation (Carpenteria, Calif.). Anti-rabbit immunoglobulins conjugated to HRP were purchased from Sigma Chemical Company (St. Louis, Mo.). Synthetic human fibrinopeptide A was purchased from Sigma Chemical Company. Rabbit antisera against human fibrinopeptide A was purchased from Nordic Immunological Laboratories (Caplstrano Beach, Calif.). Immulon II microtiter plates were purchased from Fisher Scientific (Pittsburgh, Pa.). Plasma derived human fibrinogen was provided by American Red Cross. (Rockville, Md.). O-phenylenediamine-2HCl (OPD) tablets were purchased from Abbott Laboratories (Chicago, Ill.). Metal enhanced DAB substrate was purchased from Pierce Chemical Company (Rockford, Ill.). Centricon diafilters were purchased from Amicon (Bedford, Mass.). 4–15% gradient phast-gels were purchased from Pharmacia Biotech (Piscataway, N.J.). Nitrocellulose papers (40 microns pore size) were purchased from Sigma Chemical Company. DEAE-Fast flow sepharose was purchased from Pharmacia Biotech (Piscataway, N.J.). DEAE chromatography was performed with Pharmacia C-10 columns (15 cm×1 cm), a Masterflex peristaltic pump, a Knauer spectrophotometer, and a Rainin data acquisition system were used to monitor chromatography. All other reagents were purchased from Sigma Chemical Company at the best grade available. Columns were kept at 40 C with a Lauda Super RMT water cooler.

A. Separation of Transgenic Human FIB from Host Mouse FIB

Figure 8:
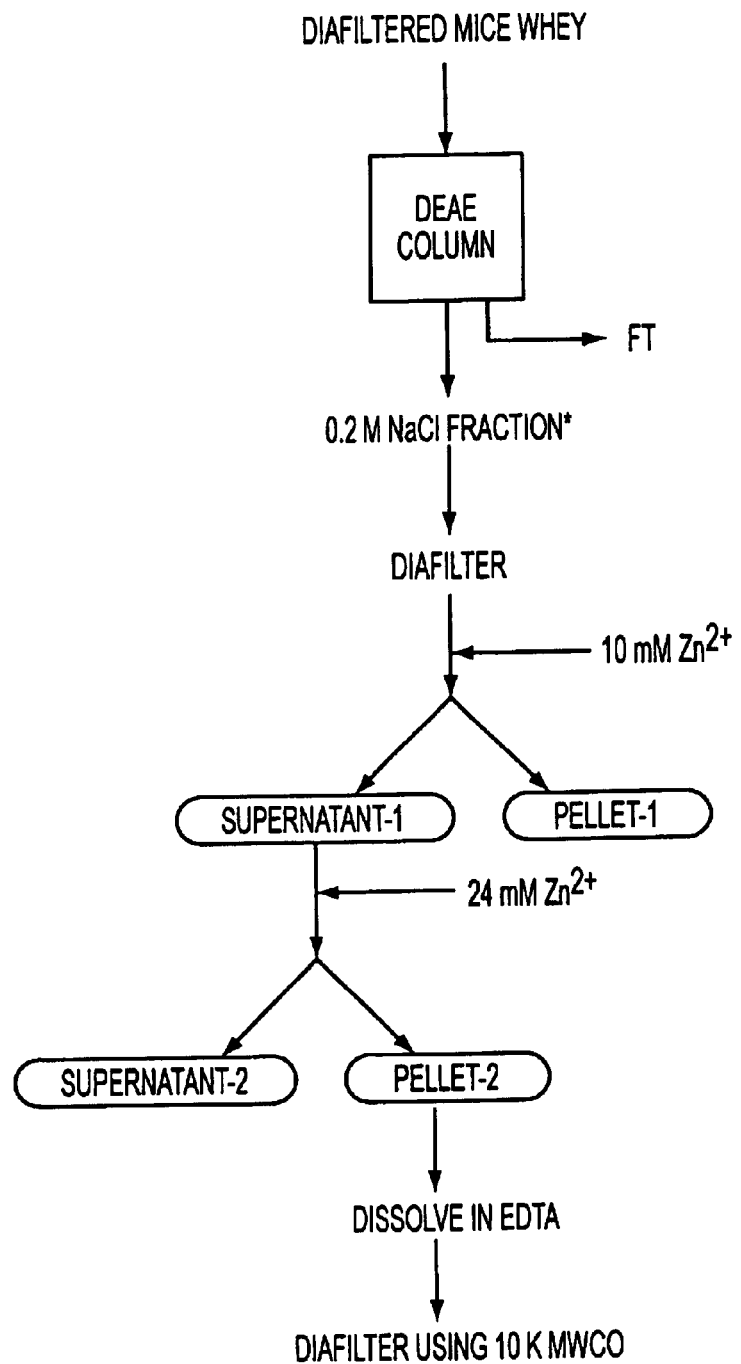
FIG. 8 is a schematic of the means for separating endogenous from rhFIB in mouse milk whey and plasma.

A sequence of anion exchange adsorption to reduce background protein content followed by a 2-step zinc ion-selective separation of hFIB or rhFIB from mouse FIB was done on mouse milk whey and mouse plasma samples (FIG. 8). Milk from transgenic and non-injected control mice were diluted with an equal volume of 200 mM EDTA, pH 7.0. An aliquot of milk from control (nontransgenic mice) was spiked with known hFIB to give a final concentration of 30–50 $\mu$g/ml, and diluted with 1 part EDTA. The milk:EDTA mixture was centrifuged at 4400 rpm for 45 minutes and the whey phase was separated from the top fat layer. Mouse blood was used as a positive control to measure cross-reactivity of anti-human fibrinogen antisera to mouse fibrinogen. All samples were diafiltered against TBS (25 mM Tris-HCl, 100 mM NaCl, pH 7.0) and then were fractionated on a DEAE Fast Flow Sepharose packed column at a linear velocity of 1 cm/min. The column dimensions were: 1 cm bed diameter and 6 cm in length. A fraction obtained by elution with 0.2 M NaCl fraction was diafiltered against TBS and reconstituted to the original sample volume. Using a 0.5 M $ZnCl_2$ stock solution, the zinc ion concentration in the samples was adjusted to 10 MM. This gave a visible precipitate which was separated by centrifugation at 10000 rpm (rotor diameter 6 inches) for 20 mins (pellet 1). Pellet-1 was dissolved in 100 mM EDTA, pH 7.0. Using the stock solution, the zinc concentration in the supernatant fluid was adjusted to 24 mM. The resultant precipitate was centrifuged at 10000 rpm for 10 mins and the sediment (pellet-2) was dissolved in 100 mM EDTA, pH 7.0. EDTA solutions from pellet-1 and pellet-2, as well as associated supernatant fluids, were analyzed for rhFIB by ELISA and the fractions were diafiltered against TBS.

Pellets from control mouse whey alone (no doped human fibrinogen) were dissolved to the same dilution factor as pellets from transgenic whey and human fibrinogen doped control whey. ELISA values for the dissolved transgenic whey and human fibrinogen doped control whey were 30–50 $\mu$g/ml human fibrinogen. The control (pellet-2) when reconstituted to the same volume as TG (pellet-2) or hFIB spiked control whey (pellet-2) gave a fibrinogen level of 1-2 $\mu$g/ml as measured by ELISA.

The pellet-2 of non-transgenic whey was also reconstituted to a 20-fold more-concentrated level than transgenic whey and human fibrinogen doped control whey. This 20-fold concentrated, negative control was assayed by ELISA, and the value was then 30 $\mu$g/ml human fibrinogen cross reactive equivalent signal with human fibrinogen antisera.

The dissolved pellets from transgenic whey and human fibrinogen doped control whey having 30–50 $\mu$g/ml human fibrinogen by ELISA signal were applied to a phast-gel, SDS-PAGE (1 $\mu$l sample volume applied to phastgel). A 1 $\mu$l application of the 20 fold-more concentrated, negative-control, dissolved pellet also was applied to the gel.

B. Western Blot Analysis Under Non-Reducing Conditions hFIB (reference) in assay buffer, diafiltered mouse plasma and rhFIB-rich fraction (pellet-2 of zinc separation step) of transgenic whey were mixed with non-reducing cocktail at 4:1 ratio and boiled for 5 minutes. Samples were analyzed on a 4–15% SDS-phast gel. Upon the completion of electrophoretic separation, the proteins were blotted onto a nitrocellulose membrane via "phast-gel diffusion blotting." The blot was probed for hFIB or rhFIB by a sandwich of rabbit anti-human fibrinogen antibody and anti-rabbit HRP conjugate antibody. Bound chromophore was visualized by metal enhanced DAB substrate. The results are shown in FIG. 9.

Figure 9:
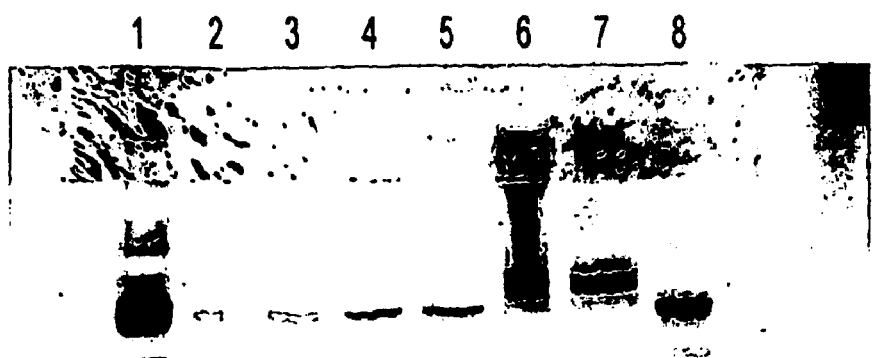
FIG. 9 shows a Western blot under non-reducing conditions of transgenic rhFIB in mouse whey and plasma.

Lanes 1 and 8 of FIG. 9 show applications of hFIB reference protein at 100 and 10 ngs. Lanes 2 and 3 shows the transgenic pellet from mouse (1-11-8) at 15 ngs. Lanes 4 and show the transgenic pellet from mouse 1-6-8 at 30 ngs. Lane 6 shows mouse plasma derivative at 2–4 $\mu$g of total protein application. Lane 8 shows pellet-2 from control whey.

The mobilities of rhFIBs under non-reducing conditions on 4–15% PAGE phast-gel from two different transgenic mice lines are similar to that of the plasma-derived hFIB reference (lanes 2–5). Intact mouse FIB from plasma (lane 6) and control whey pellet-2 (lane 7) migrated as multiple bands with a distinctly apparent higher molecular weight as compared to human FIB (lanes 1 and. 10).

C. Western Blot Analysis Under Reducing Conditions hFIB (reference protein) in assay buffer, diafiltered mouse plasma and rhFIB-rich fraction (pellet-2 of zinc separation step) of transgenic whey were mixed with reducing cocktail at 4:1 ratio and boiled for 5 minutes. Samples were analyzed on a 8–25% SDS-phast gel. Upon the completion of electrophoretic separation, the proteins were blotted onto a nitrocellulose membrane via "phast-gel diffusion blotting." The blot was probed for hFIB or rhFIB by a sandwich of rabbit anti-human FIB and anti-rabbit HRP conjugate antibodies. Bound chromophore was visualized by metal-enhanced DAB substrate. The results are shown in FIG. 10.

Figure 10:
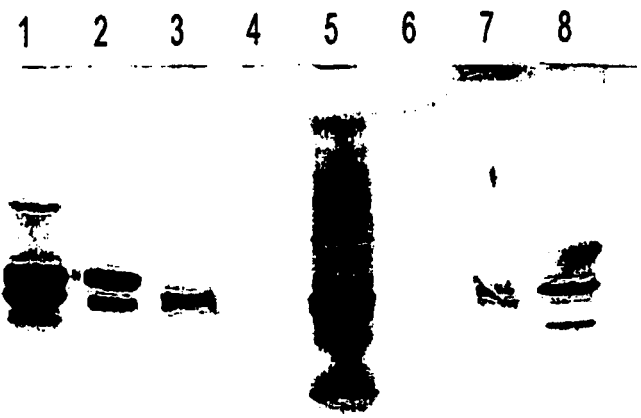
FIG. 10 shows the same experiment as in FIG. 9, except that the gel was run under reducing conditions.

Lanes 1, 2 and 3 of FIG. 10 show applications of hFIB reference at 100, 50 and 10 ngs. Lane 4 shows mouse plasma derivative (i.e. diafiltered 0.2 M NaCl eluate from DEAE FF Sepharose column). Lane 5, 6, 7 and 8 show applications of transgenic whey pellet-2 at 60, 30, 15 and 7.5 ngs.

Under reduced conditions, $\alpha$, $\beta$ and $\gamma$ chains of reference hFIB from human plasma are clearly visible (lanes 1–3). Fibrinogen chains from mouse plasma (lane 4) have lower apparent molecular weights than human FIB, but different than rhFIB. Partially purified material from transgenic whey has three chains with lower apparent molecular weights than hFIB (lanes 5–8), but a higher molecular weight than mouse fibrinogen. The $\alpha,\beta$ chains of rhFIB show up with greater intensity than the $\gamma$ chain.

D. Thrombin Assay

Diafiltered rhFIB-rich fractions from the zinc selective separation steps were suspended in 50 mM imidazole, 150 mM NaCl, 30 mM CaCl$_{21}$ pH 8.0. Human thrombin was added to a final concentration of 4 U/ml and the samples were incubated at 37° C. for 24 hours. Cloudy clot-like precipitates were clearly visible in TG (pellet-2), hFIB-spiked NTG (pellet-2), but not in control whey (pellet-2) after treated with thrombin. The clots were boiled for 3 mins and centrifuged at 10000 rpm for 10 minutes. The clot pellets were dissolved in reducing cocktail buffer. Assay supernatant was lyophilized and reconstituted to ⅒th the initial reaction volume. Supernatant was assayed for any residual fibrinogen and/or fibrin by ELISA. The level of FPA in the concentrated supernatants were determined by EIA technique.

e. Western Blot Analysis After Treatment of Fibs with Human Thrombin

Samples were taken before the addition of thrombin (Time=0 mins) and the clot after polymerization were dissolved in reducing buffer. Samples were analyzed on a 8–25% phast gel in the presence of SDS. The results are shown in FIG. 11.

Figure 11:
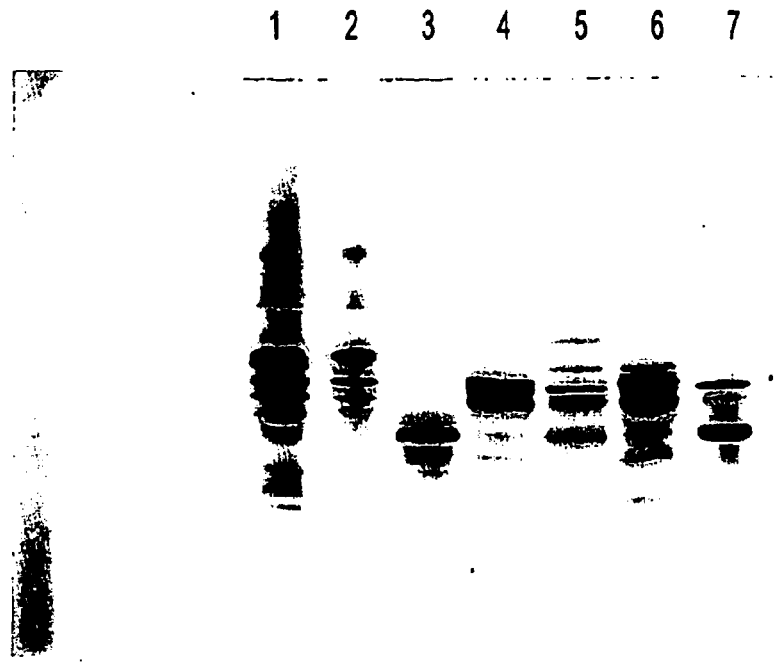
FIG. 11 shows an SDS-PAGE separation of rhFIB after digestion with thrombin.

Lanes 1 and 2 of FIG. 11 show human fibrinogen reference protein in buffer at concentrations of 50 and 10 ngs before the addition of thrombin. Lane 3 shows the dissolved clot generated from hFIB at an initial concentration of 10 ng. Lane 4 shows trangenic whey pellet-2 FIB (30 ng applied to gel) before addition of thrombin. Lane 5 shows dissolved clot generated from transgenic whey pellet-2 FIB. Lane 6 shows mouse plasma derivative (30 ng total FIB cross reactive signal by ELISA, 1000 ng mouse FIB by silver-stain analysis using SDS-PAGE). Lane 7 shows samples from the incubation of mouse plasma derivative FIB with thrombin; this precipitate is not the cloudy gel-like precipitate seen with TG whey (pellet-2) and hFIB spiked control whey (pellet-2).

The Western analysis under reducing conditions of the hFIB reference protein shows three distinct chains, and the dissolved clot resulting from thrombin digestion shows three chains with an apparent lower molecular mobility under reduced conditions. Release of fibrinopeptide A from the α chain by incubation with thrombin results in a lower apparent molecular of the α chain. Dissolved clots from transgenic whey (pellet-2) under reducing conditions gave two distinct bands with lower apparent molecular weights when compared to rhFIB before addition of thrombin. A mouse plasma sample gave bands which were reactive to FIB antisera and had lower apparent molecular weights than reduced hFIB.

F. Assay of Fibrinopeptide a After Thrombin Digestion of rhFIB

The levels of FPA in the concentrated samples were determined by an EIA technique. Immobilon AV membranes were wetted in imidazole buffer for 10 minutes and dried for 60–90 minutes at room temperature. FPA standards ranging from 0.2–0.125 mg/ml and assay supernatant fluids were applied as 1 μl spots onto a pre-wetted Immobilon AV membrane for the purpose of covalent immobilization. Smaller peptides such as FPA (MW 1,800) are kinetically favored for immobilization over larger peptides or milk proteins with molecular weights in excess of 10,000. The spots were allowed to dry at room temperature and the membrane was blocked with 0.5% casein for 2 hours at the same temperature. Covalently bound FPA was detected with a sandwich of rabbit anti-FPA and anti-rabbit/HRP conjugate antibodies. Bound chromophore was detected with metal enhanced DAB substrate. The spots were scanned on a Shimazdu Densitometer at 270 nm. The results are summarized in Table 8.

FPA standards ranging from 200-6.25 ngs were applied to enzyme immunoassay (EIA) membranes for reference signal curves. Transgenic whey derivatives that had been selectively enriched for recombinant human fibrinogen by precipitation, were similarly applied and analyzed for the releaste of FPA before and after human trombin treatment for 24 hours. Analogously prepared and then thrombin treated, non-transgenic whey derivatives were also compared in the same EIA assay. These results are summarized in Table 8 entitled "Thrombin treatment of Fibrinogen Samples.

The yield of FPA from hFIB in assay buffer treated with thrombin was 100±10% based on three independent trials (Table 1). No detectable amount of FPA was released from control whey (pellet-2) treated with thrombin. 1,000 ng of mouse FIB from mouse plasma (equivalent to 25 ngs of FIB cross reactive signal) gave a FPA yield of 5%. Transgenic whey (pellet-2) and hFIB spiked control whey (pellet-2) when treated with thrombin released FPA in the supernatant fluid, and no residual rhFIB or hFIB was detected in the supernatant fluid by ELISA. The yield based on the amount of FPA released from TG whey (pellet-2) and hFIB spiked control whey (pellet-2) is estimated to be 60±8% and 75±9% respectively based on three independent trials. A 1/1 molar ratio of FPA to fibrinogen is assumed in the calculation.

TABLE 8

Thrombin Treatment of Fibrinogen Samples

| Sample (supernatant) | Fibrinogen μg/ml (ELISA) | | % FPA yield |
|---|---|---|---|
| | T = 0 min | T = 24 hours | T = 24 hours |
| hFIB (buffer) | 100 | 0.1 | 100 ± 5 |
| hFIB (buffer) | 10 | n.d. | 100 ± 10 |
| Spiked NTG whey (pellet-2) | 50 | 0.1 | 75 ± 9 |
| TG whey (pellet-2) | 30 | n.d. | 60 ± 8 |
| NTG whey (pellet-2) | 30 | n.d. | n.d. |
| Mouse plasma | 30 | n.d. | 5 |

G. Summary

Mouse FIB was found to have a higher apparent molecular weight under nonreducing conditions both by silver-stained SDS-PAGE gels and corresponding Western blot analyses using polyclonal anti-human fibrinogen antisera, than human FIB. In contrast, the separate α, β and γ chains of the mouse plasma FIB, as detected by gel analyses under reducing conditions, had slightly lower apparent molecular weights (about 1–5 kDa per chain) than human FIB. These data from reduced and nonreduced analyses indicate that the disulfide bridging and resultant SDS-sensitive conformation of the assembled mouse FIB is different than for the human counterpart. Furthermore, the cross-reactivity to anti-human fibrinogen signal was about 40-fold less than human or rhFIB in both ELISA and Western analysis assuming about 2g/l mouse FIB in mouse plasma reference as detected by silver stain gel. Mouse plasma FIB was also found in transgenic and control mouse milks at about 200 to 300 μg/ml. After purification processing, all Zn-derived pellet-2 from nondoped control whey or mouse plasmas exhibited no detectable clot formation nor FPA formation after treatment with human thrombin. But lower apparent molecular weight FIB chain reaction products may have been produced by treatment with thrombin under conditions of about 20-fold higher initial concentration of FIB substrate than used for human FIB-doped whey derivative or rhFIB samples. Both the absence of FPA and an obvious clot after treatment with human thrombin was expected. While mouse FIB undoubtedly has regions of well-conserved sequence homology, both the mouse FPA sequence and the nature of the digestion by human thrombin (slower reaction kinetics due to site specificity of human thrombin for human fibrinogen) is likely to be different. The 40-fold lower cross-reactivity of mouse FIB with anti-hFIB antisera is additional evidence of the differences in mouse and human fibrinogens.

The FIB doped into whey and recovered by the above purification process was readily converted to fibrin by the addition of human thrombin. A normal fibrin clot and stoichiometric release of FPA into the supernatant solution was found after treatment with thrombin. A characteristically lower apparent molecular weight of the fibrin chains from the clot was found relative to the starting FIB precursor chains.

The assembled rhFIB possessed an apparent molecular weight similar to that of human FIB reference standard. The physicochemical properties of the rhFIB were similar to those of hFIB as reflected by the similar partitioning during the $Zn^{2+}$ selective purification scheme. $Zn^{2+}$ is a coordinate covalent bonder of proteins primarily through access to proximally portioned, surface positioned histidine residues, and thus the tertiary conformation of the proteins is changed by the formation of $Zn^{2+}$ bonds Lonnerdal (1982), supra. Changes in tertiary confirmation by Zn-bonding are reflected in a Zn-concentration dependent manner by the precipitation (loss of solubility). Similar amounts of recombinant and human FIB precipitated out at 24 mM $Zn^{2+}$ and as found in pellet-2. The sensitivity of this technique is seen with the structurally related mouse FIB which did not precipitate to any significant degree at this same level of Zn. Thus, the presentation of surface histidine residues is similar between human and recombinant FIB, but much different for mouse FIB. The separate chains of rhFIB will slightly lower apparent molecular weights than non-recombinant human FIB due possibly to glycosylation of β and γ chains. The reactivity to anti-human fibrinogen antisera of purified recombinant fibrinogen was generally equivalent to human fibrinogen.

The rhFIB recovered from the transgenic was readily converted to fibrin by the addition of human thrombin and in a manner similar to that of human FIB reference protein. A normal human fibrin clot and stoichiometric release of FPA into the supernatant solution was found after treatment with human thrombin. The yield of FPA detected by EIA after treatment with human thrombin for rhFIB fibrinogen was equivalent to that obtained with human FIB. As the yields of fibrin from human or recombinant fibrinogens were high, the residual milk proteins present after purification did not interfere significantly with the thrombin-fibrinogen reaction. A characteristically lower apparent molecular weight of the recombinant human fibrin chains from the clot was found relative to the starting FIB precursor chains.

In summary, these analyses have shown that the rhFIB made has a genuine and native structure with respect to biological activity. This was evidenced by its simultaneous consumption and conversion into a normal fibrin clot while acting as a substrate during enzymatic reaction with human thrombin, stoichiometric release of native fibrinopeptide A upon formation of fibrin, lower relative molecular weights of resultant fibrin polypeptide chains relative to FIB precursors, its coordinate chemical bonding properties with Zn, and its equivalent reactivity with human antisera relative to a human FIB reference protein.

What is claimed is:

1. A method for producing biologically active fibrinogen comprising:

providing a transgenic non-human mammal whose genome comprises a first DNA segment encoding a first DNA encoding a heterologous fibrinogen Aα chain, a second DNA segment encoding a second DNA encoding a heterologous fibrinogen Bβ chain, and a third DNA segment encoding a third DNA encoding a heterologous fibrinogen γ chain, wherein each chain is derived from the same species, and wherein each of said first, second and third segments is operably linked to a cis-acting, expression promoter-containing regulatory sequence required for its expression in a mammary gland of a female transgenic non-human mammal;

allowing the expression of said first, second and third DNA segments and the production of milk containing biologically active fibrinogen in said female mammal;

collecting milk from said female mammal; and recovering the biologically active fibrinogen from the milk.

2. The method according to claim 1, wherein said transgenic non-human mammal is selected from the group consisting of a rodent, rabbit, sheep, pig, goat and cattle.

3. The method according to claim 2, wherein said transgenic non-human mammal is a sheep.

4. The method according to claim 1, wherein said transgenic non-human mammal is a cow.

5. The method according to claim 1, wherein said promoter to which each of said first, second and third DNA segments is operably linked is selected from the group consisting of casein, β-lactoglobulin, α-lactalbumin and whey acidic protein gene promoters.

6. The method according to claim 5, wherein said promoter is a β-lactoglobulin promoter.

7. The method according to claim 5, wherein said promoter is a casein promoter.

8. The method according to claim 5, wherein said promoter is a whey acidic protein gene promoter.

9. The method according to claim 1, wherein said fibrinogen is human fibrinogen.

10. The method according to claim 1, wherein said first, second, and third DNA segments comprises an intron.

11. A method for producing biologically active fibrinogen comprising:

providing a first DNA segment encoding a heterologous fibrinogen αa chain, a second DNA segment encoding a heterologous fibrinogen Bβ chain; and a third DNA segment encoding a heterologous fibrinogen γ chain, wherein each chain is from the same species, and wherein each of said first, second and third segments is operably linked to a promoter-containing regulatory sequence required for its expression in the mammary gland of a female transgenic non-human mammal;

introducing said DNA segments into a fertilized egg of a non-human mammalian species heterologous to the species of origin of said fibrinogen chains;

inserting said egg into an oviduct or uterus of a female of said mammalian species to obtain a transgenic non-human mammal whose genome comprises said DNA segments;

breeding said mammal to produce female progeny that express said first, second and third DNA segments and produce milk containing biologically active fibrinogen encoded by said segments;

collecting milk from said female progeny; and recovering the biologically active fibrinogen from the milk.

12. The method according to claim 11, wherein said transgenic non-human mammal is selected from the group consisting of a rodent, rabbit, sheep, pig, goat and cattle.

13. The method according to claim 11, wherein said species into which said DNA segments is introduced is a sheep.

14. The method according to claim 11, wherein said species into which said DNA segments is introduced is a cow.

15. The method according to claim 11, wherein said non-human mammal is a cow.

16. The method according to claim 11, wherein said first, second, and third DNA segments comprises an intron.

17. The method according to claim 11, wherein each of said first, second and third DNA segments is operably linked to a transcription promoter selected from the group consisting of casein, β-lactoglobulin, α-lactalbumin and whey acidic protein gene promoters.

18. A method according to claim 11, wherein said first, second and third DNA segments are expressed under the control of a β-lactoglobulin promoter.

19. The method according to claim 11, wherein said first, second and third DNA segments are expressed under the control of a casein promoter.

20. The method according to claim 11, wherein said first, second and third DNA segments are expressed under the control of a whey acidic protein gene promoter.

21. The method according to claim 11, wherein said introducing step comprises injecting said first, second and third DNA segments into a pronucleus of said fertilized egg.

22. The method according to claim 11, wherein said fibrinogen is human fibrinogen.

23. The method according to claim 11, wherein said introducing step comprises injecting said first, second and third DNA segments into a pronucleus of a fertilized egg and inserting said egg into an oviduct of a pseudopregnant female to produce a female transgenic non-human mammal whose genome comprises said DNA segments, wherein said egg and said pseudopregnant female are of the same species.

24. The method of claim 23, wherein said female mammal is a sheep.

25. The method of claim 23, wherein said female mammal is a cow.

26. A transgenic non-human mammal, wherein the genome of said mammal comprises:

a first DNA segment encoding a heterologous fibrinogen Aα chain, a second DNA segment encoding a heterologous fibrinogen Bβ chain, a third DNA segment encoding a heterologous fibrinogen γ chain, and further wherein each chain is derived from the same species and is operably linked to a promoter-containing regulatory sequence required for its expression in the mammary gland of a host female mammal, wherein expression of said DNA segments results in the production of recoverable quantities of biologically active fibrinogen from milk of a female of said non-human mammal.

27. The non-human transgenic mammal according to claim 26, wherein said non-human mammal is selected from the group consisting of a rodent, rabbit, sheep, pig, goat and cattle.

28. The non-human transgenic mammal according to claim 27, wherein said non-human mammal is a sheep.

29. The non-human transgenic mammal according to claim 26, wherein said non-human mammal is a cow.

30. The non-human transgenic mammal according to claim 26, wherein each of said first, second and third DNA segments is operably linked to a transcription promoter selected from the group consisting of casein, β-lactoglobulin, α-lactalbumin and whey acidic protein gene promoters.

31. The non-human transgenic mammal according to claim 26, wherein said first, second and third DNA segments are expressed under the control of a β-lactoglobulin promoter.

32. The non-human transgenic mammal according to claim 26, wherein said first, second and third DNA segments are expressed under the control of a casein promoter.

33. The non-human transgenic mammal according to claim 26, wherein said first, second and third DNA segments are expressed under the control of a whey acidic protein gene promoter.

34. The non-human mammal produced according to claim 26, wherein said mammal is female.

35. The non-human mammal produced according to claim 26, wherein said mammal is male.

36. A process for producing a transgenic non-human mammal comprising:

providing a first DNA segment encoding a first DNA encoding a heterologous fibrinogen Aα chain, a second DNA segment encoding a second DNA encoding a heterologous fibrinogen Bβ chain, and a third DNA segment encoding a third DNA encoding a heterologous fibrinogen γ chain, wherein each chain is derived from the same species, and wherein each of said first, second and third segments is operably linked to a promoter-containing regulatory sequence required for its expression in a mammary gland of a host female mammal;

introducing said DNA segments into a fertilized egg of a non-human species heterologous to the species of origin of said fibrinogen chains;

inserting said fertilized egg into an oviduct or uterus of a female of said mammalian species; and allowing said fertilized egg to develop thereby producing a transgenic non-human mammal whose genome comprises said first, second and third DNA segments, wherein female progeny of said mammal express said DNA segments in a mammary gland to produce biologically active fibrinogen in recoverable quantities in the milk of said female progeny.

37. The process according to claim 36, wherein said mammal is female.

38. The process according to claim 36, wherein said mammal is male.

* * * * *

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccccagctgc agccatgaag                                              20

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccccagggat atccctgcag ccatgaag                                     28

<210> SEQ ID NO 3
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 3
gctaggtacc atgttttcca tgaggatcgt                                    30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cagtggtacc ctagacaggg cgagatttag                                    30

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gctaggtacc atgaaaagaa tggtttcgtg                                    30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cagtggtacc ctattgctgt gggaagaagg                                    30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gctaggtacc atgagttggt ccttgcaccc                                    30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cagtggtacc ttaaacgtct ccagcctgtt                                    30

<210> SEQ ID NO 9
<211> LENGTH: 25
<212> TYPE: DNA
<213> ORGANISM: Artificial Sequence
<220> FEATURE:
```

-continued

```
<223> OTHER INFORMATION: Description of Artificial Sequence: Synthetic
      primer

<400> SEQUENCE: 9
ctgtgtggcc aagaaggaag tgttg                                          25

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gatgtctttc cacaaccctt gggc                                           24

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cccgatagcc acctcctctg atg                                            23

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cctggacttc aaagtagcag cgtc                                           24
```